(12) United States Patent
Rettedal et al.

(10) Patent No.: US 12,340,885 B2
(45) Date of Patent: Jun. 24, 2025

(54) COMPUTERIZED SYSTEMS AND METHODS FOR LIVESTOCK MANAGEMENT

(71) Applicant: ST Reproductive Technologies, LLC, Navasota, TX (US)

(72) Inventors: Nicholas P. Rettedal, Berthoud, CO (US); Matheus Dasuke, College Station, TX (US)

(73) Assignee: ST Reproductive Technologies, LLC, Navasota, TX (US)

( * ) Notice: Subject to any disclaimer, the term of this patent is extended or adjusted under 35 U.S.C. 154(b) by 215 days.

(21) Appl. No.: 17/455,790

(22) Filed: Nov. 19, 2021

(65) Prior Publication Data

US 2023/0162829 A1    May 25, 2023

(51) Int. Cl.
*G16H 20/10* (2018.01)
*G16H 10/60* (2018.01)

(52) U.S. Cl.
CPC ............ *G16H 20/10* (2018.01); *G16H 10/60* (2018.01)

(58) Field of Classification Search
None
See application file for complete search history.

(56) References Cited

U.S. PATENT DOCUMENTS

| | | | |
|---|---|---|---|
| 9,636,273 B1 | 5/2017 | Harris | |
| 10,231,644 B2 | 3/2019 | Rettedal et al. | |
| 10,297,032 B2 | 5/2019 | Hanina et al. | |
| 10,306,868 B2 | 6/2019 | Rettedal et al. | |
| 10,528,911 B1 | 1/2020 | Laster | |
| 10,548,509 B2 | 2/2020 | Rettedal et al. | |
| 11,206,811 B2 | 12/2021 | Rettedal et al. | |
| 2008/0097809 A1 | 4/2008 | Stroman et al. | |
| 2012/0182145 A1* | 7/2012 | Jameson | A01K 11/008 340/539.13 |
| 2014/0288962 A1 | 9/2014 | Krzanowski et al. | |
| 2015/0097668 A1 | 4/2015 | Florczak | |
| 2016/0198680 A1* | 7/2016 | Mobley | A01K 11/008 340/573.3 |

(Continued)

OTHER PUBLICATIONS

Zuper ("5 Ways Geofencing Can Shave Hours off Your Field Service Operations," Zuper Blog article, Mar. 17, 2021, https://www.zuper.co/blog/geofencing-in-field-service) (Year: 2021).*

(Continued)

*Primary Examiner* — Christopher B Tokarczyk
(74) *Attorney, Agent, or Firm* — Ryan Christensen; Hashim Rahman

(57) ABSTRACT

Various examples described herein are directed to systems and methods for providing a treatment substance to an animal. A server may receive from a user computing device an indication of the animal to be treated. The server may access an indication of a treatment substance to be provided to the animal and receive from the user computing device, a first current location of the user computing device. The server may determine that the first current location of the user computing device is more than a threshold distance from an expected location of the animal and, based on the determining that the first current location of the user computing device is more than a threshold distance from the expected location of the animal, send an alert message to an administrative user device.

8 Claims, 17 Drawing Sheets

(56) References Cited

U.S. PATENT DOCUMENTS

2019/0380311 A1* 12/2019 Crouthamel ......... A01K 11/004

OTHER PUBLICATIONS

Tedeschi et al. ("Advancements in sensor technology and decision support intelligent tools to assist smart livestock farming," Journal of Animal Science, vol. 99, Issue 2, Feb. 2021) (Year: 2021).*
Zuper, "5 Ways Geofencing Can Shave Hours off Your Field Service Operations", Zuper Blog 1-20 article, Mar. 17, 2021. Retrieved on Jan. 21, 2023. https://www.zuper.co/blog/geofencing-in-field-service.
International Search Report and Written Opinion issued on Feb. 22, 2023 in related PCT Appl. No. PCT/US2022/049963.
Examination report in related Australian Application No. 2022394328, 3 pages, dated: Mar. 25, 2024.

* cited by examiner

FIG. 15

COMPUTERIZED SYSTEMS AND METHODS FOR LIVESTOCK MANAGEMENT

TECHNICAL FIELD

This document generally relates to methods and systems for use with computer systems and other devices. More particularly, this document relates to ways of configuring and operating computing devices and systems to facilitate the management of livestock.

BACKGROUND

Livestock animals, including cattle, sheep, pigs, etc., are typically monitored by livestock technicians or other similar users. The livestock technicians determine whether the animal requires treatment for illness or other conditions and provide appropriate treatment.

BRIEF DESCRIPTION OF DRAWINGS

The present disclosure is illustrated by way of example and not limitation in the following figures.

FIGS. 10-15 are screen shots showing various screens that may be displayed at a user computing device as part of the GUI described herein.

DETAILED DESCRIPTION

Figure 1:
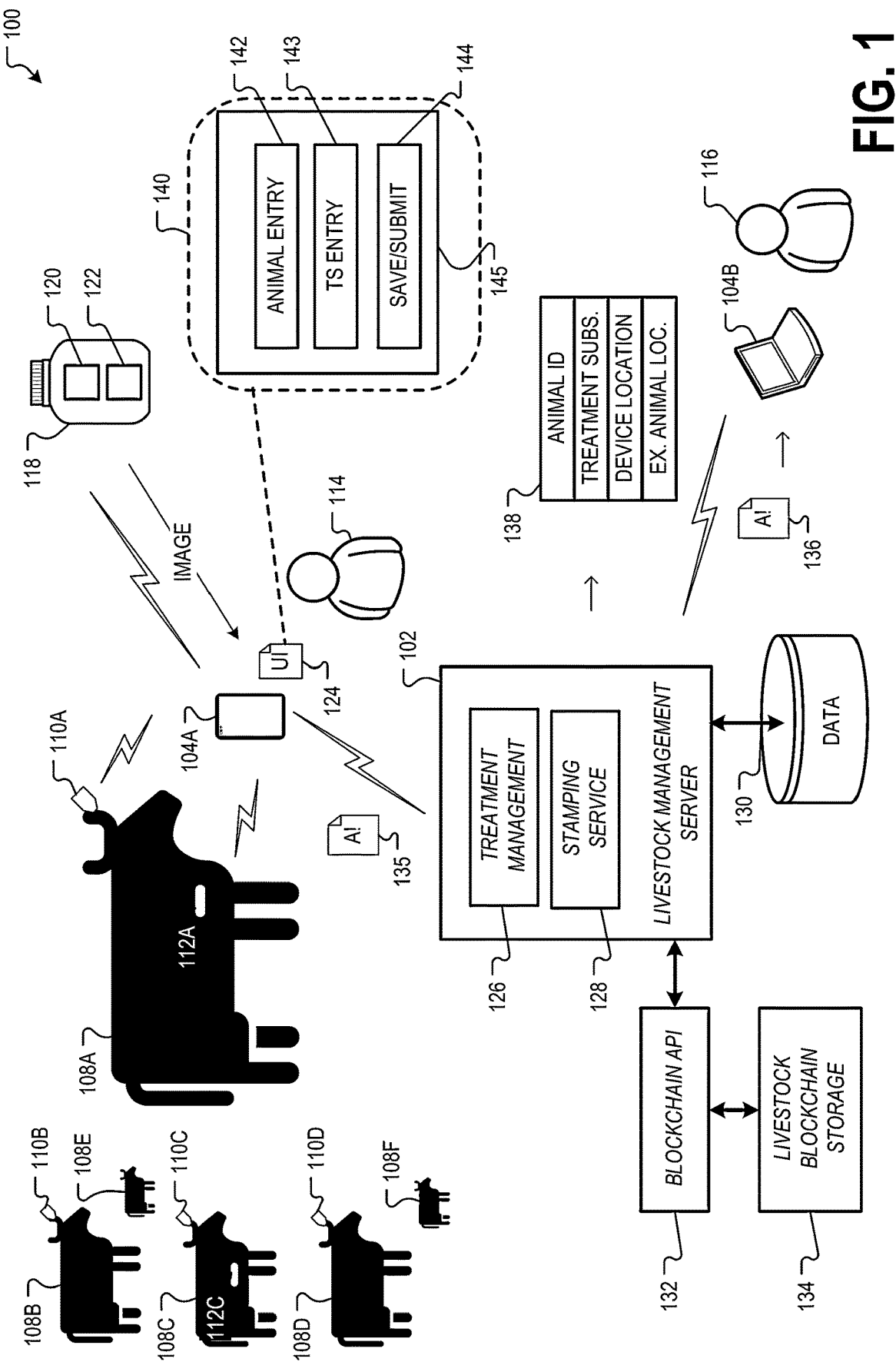
FIG. 1 is a diagram showing one example of an environment for implementing a computerized livestock management system.

Livestock technicians often provide treatment substances to animals. Treatment substances can include, for example, medications, such as antibiotics, dietary supplements, and the like. In some examples, treatment substances can include medical supplies, such as sutures, bandaging, and the like. Also, in some examples, treatment substances can include substances associated with artificial insemination, such as semen. A livestock technician may receive a quantity of treatment substance from a livestock pharmacy or other similar depot and travel to a holding pen, feeding area, or other location frequented by livestock to administer the treatment substance to one or more animals.

Sometimes, it can be a challenge to track treatment substances provided to animals. For example, a livestock technician may check out multiple doses of a treatment substance and provide the doses to animals at one or more pens or other suitable locations at a farm, ranch, or other similar facility. In some examples, such as when the treatment substance is a medication, the livestock technician may not know which animals will receive treatment substances at the time that the substances are checked-out.

In some examples, livestock treatment substances and/or livestock technician activities can be tracked with a pen-and-paper arrangement. The livestock treatment technician may keep a paper record of which treatment substances are provided to specific animals. A pen-and-paper arrangement, however, can lead to various problems. For example, in a farm or ranch setting, paper records can become wet, soiled, or otherwise degraded, leading to the loss of data. Also, paper records may be poorly kept or even falsified in some circumstances. For example, when a paper record sheet is lost, the livestock technician may need to recreate the sheet after-the-fact.

In other arrangements, livestock treatment substances and/or livestock technician activities are tracked using computer-implemented spreadsheets, such as Microsoft Excel spreadsheets. Although computer-implemented, spreadsheets and similar arrangements may present additional challenges. For example, mobile interfaces to spreadsheets tend to be difficult to use. This can lead to errors in data entry and/or may cause livestock technicians to enter activity and/or treatment substance data after the fact, when errors may be more likely and record falsification more difficult to detect.

These and other challenges may be addressed with systems and methods disclosed herein for providing treatment substances to animals. A livestock management server may be in communication with one or more user computing devices. The user computing devices may be in the possession of livestock technicians, who carry the user computing devices with them while tending to animals. When a livestock technician is to provide a treatment activity to an animal, the livestock technician provides an indication of the animal and an indication of the treatment activity to the user computing device. For treatment activities that also include administering a treatment substance to the animal, an indication of the treatment substance is also provided. The user computing device may be programmed to determine its current location and provide the current location to the livestock management server along with the indication of the animal, the indication of the treatment activity, and the indication of the treatment substance (if any).

The user computing device and/or the livestock management server may be configured to compare the current location of the user computing device to an expected location of the indicated animal. If the current location of the user computing device is more than a threshold distance from the expected location of the animal, it may indicate a potentially erroneous and/or falsified record. In some examples, the livestock management server may send an alert message to an administrative user device. The alert message may describe the mismatch. The alert message may include a prompt to the administrative user to address the mismatch, for example, by contacting the livestock technician who submitted the record.

FIG. 1 is a diagram showing one example of an environment 100 for implementing a computerized livestock management system. The environment 100 includes a livestock management server 102 and user computing devices 104A, 104B. The environment 100 also includes animals 108A, 108B, 108C, 108D, 108E, 108F as well as users 114, 116. User 114 may be a livestock technician user who tends to animals 108A, 108B, 108C, 108D, 108E, 108F as described herein. In some examples, the user 116 is an administrative user. The user 116, for example, may track records of livestock technician activities and/or treatment substances provided by the livestock management.

The livestock management server 102 may communicate with the user computing devices 104A, 104B, as described herein, to receive data describing the activities of the livestock technician user 114 and/or data describing treatment substances provided to the various animals 108A, 108B, 108C, 108D, 108E, 108F. The livestock management server 102 includes one or more computing devices that may be at a common geographic location or may be distributed across multiple geographic applications.

The livestock management server 102 includes a treatment management service 126 and a stamping service 128. The stamping service 128 may receive data describing activities of the livestock technician user 114 and/or data describing treatment substances provided to the various animals 108A, 108B, 108C, 108D, 108E, 108F and generate corresponding records. In some examples, the stamping service 128 generates a timestamp data indicating when the data was received from the livestock technician user 114 (e.g., via the user computing device 104A). The treatment management service 126 may be configured to manage records of treatment activities performed by livestock technicians and/or records of treatment substances. For example, the treatment management service 126 may manage and/or track inventories of treatment substances, as described herein. The treatment management service 126 may store to and/or retrieve records from a database 130 and/or a livestock blockchain storage 134 (e.g., via a blockchain API 132) as described in more detail herein.

The treatment management service 126 and stamping service 128 may be implemented, for example, as software executing at the livestock management server 102. For example, the treatment management service 126 and/or stamping service 128 may be implemented as applications, web services, or in other suitable formats.

The users 114, 116 may utilize user computing devices 104A, 104B. The user computing devices 104A, 104B may be or may include any suitable computing device or devices such as, for example, smart phones, tablet computers, laptop computers, smart watches, etc. The user computing devices 104A, 104B may comprise input/output (I/O) devices for providing a graphical user interfaces (GUIs) to the users 114, 116. For example, the user computing device 104A may provide a GUI 124 to the livestock technician user 114. The user computing device 104A may generate the GUI 124, for example, via an application executing at the user computing device 104A. In some examples, the user computing device 104A executes a web application in communication with the livestock management server 102. The livestock management server 102 may serve the GUI 124 to the user computing device 104A via the web application.

The user computing device 104B may provide alert message 136 including record data 138, as described in more detail herein. In some examples, one or more of the user computing devices 104A, 104B is or comprises a display that is configured to be worn on the user's head, such as a heads-up display, smart glasses display or similar display.

In the example of FIG. 1, the user computing device 104A provides the GUI 124 to the livestock technician user 114. A breakout window 140 shows an example GUI screen 145 of the GUI 124 including GUI elements 142, 143, 144 described in more detail herein.

In some examples, the user computing device 104A is in communication with various other devices to collect data about treatment activities and/or treatment substances administered to the animals 108A, 108B, 108C, 108D, 108E, 108F. For example, the user computing device 104A may collect data describing an animal to be treated. Data describing an animal may be received in various different ways. In some examples, the GUI 124 includes one or more animal entry fields where the livestock technician user 114 enters data identifying an animal 108A, 108B, 108C, 108D, 108E, 108F at an animal entry field 142. The livestock technician user 114 may read a serial number or other identifier of an animal 108A, 108B, 108C, 108D, 108E, 108F from a tag 110A, 110B, 110C, 110D affixed to the animal or other identifier on or associated with the animal 108A, 108B, 108C, 108D, 108E, 108F. The livestock technician user 114 may provide the read identifier to user computing device 104A via the animal entry field 142.

In other examples, the user computing device 104A may communicate with a tag 110A, 110B, 110C, 110D, bolus 112A, 112C, or another device affixed to, present in, or otherwise associated with an animal 108A, 108B, 108C, 108D, 108E, 108F. In some examples, the user computing device 104A is in wireless communication with a tag 110A, 110B, 110C, 110D using a short-range wireless communication medium. For example, some or all of the tags 110A, 110B, 110C, 110D may be configured to transmit identifying information about the animal 108A, 108B, 108C, 108D wearing the tag. Example short range wireless communication mediums that may be used include radio frequency identifier (RFID), Near Field Communication (NFC), Bluetooth®, and/or the like.

In some examples, one or more of the tags 110A, 110B, 110C, 110D comprises a radio frequency identifier (RFID) device. The user computing device 104A may comprise or be in communication with an RFID reader to wirelessly communicate with the various tag or tags 110A, 110B, 110C, 110D. In other examples, the user computing device 104A and one or more of the tags 110A, 110B, 110C, 110D may comprise components for utilizing other short range wireless communication mediums, as described herein.

In some examples, the user computing device 104A is in communication with one or more boluses 112C, 112D. A bolus, such as the boluses 112C, 112D, may be in vivo devices present inside the animals 108A, 108C. For example, the boluses 112A, 112C may have been ingested by the respective animals 108A, 108C. The boluses 112C, 112D may include one or more sensors, such as temperature sensors, pH sensors, etc. The boluses 112C, 112D may also include a wireless communication circuit configured to communicate with the user computing device 104A. In some examples, the boluses 112C, 112D are configured to communicate via a short-range wireless communication medium such as, for example, RFID, NFC, Bluetooth®, and/or the like.

The user computing device 104A may also receive data describing a treatment activity and/or treatment substance provided to an animal 108A, 108B, 108C, 108D, 108D, 108F. In some examples, data describing a treatment activity and/or treatment substance is provided via the GUI 124 by the livestock technician user 114. For example, the livestock technician user 114 may enter information regarding a treatment substance administered to an animal via one or more treatment substance entry fields 143 of the example GUI screen 145. The user computing device 104A may be programmed, in some examples, to assist the livestock technician in determining a dose and/or administering the treatment substance. For example, the user computing device 104A may prompt the livestock technician user 114 to provide the animal's weight and may calculate a treatment substance dose based on the weight. In other examples, the user computing device 104A may access the animal's weight (e.g., from the livestock management server 102) based on the identity of the animal.

In some examples, the user computing device 104A obtains data regarding treatment substances by interacting with a treatment substance container 118. In the example of FIG. 1, the treatment substance container 118 is a bottle, although other suitable containers may be used including, for example, vials, bags, cassettes, and the like. In some examples, the treatment substance container 118 includes graphical code 122, such as a bar code, a Quick Response (QR) code, or other suitable graphical code. The user computing device 104A may capture an image of the graphical code 122 and decode the image to identify information about the treatment substance. The information about the treatment substance may include, for example, an identity of the treatment substance, a dose size of the treatment substance, and/or the like.

Some treatment substance containers 118 include a wireless communication circuit 120. The wireless communication circuit 120 is configured to communicate information about the treatment substance to the user computing device 104A, for example, via a short-range wireless communication medium such as, for example, RFID, NFC, Bluetooth®, and/or the like. The information about the treatment substance may include, for example, an identity of the treatment substance, a dose size of the treatment substance, and/or the like.

The livestock technician user 114 may determine to perform a treatment activity to an animal 108A. The livestock technician user 114 may determine to perform a treatment activity in any suitable manner. In some examples, treatment activities are scheduled. For example, colostrum feedings may occur for calves at predetermined times. In another example, artificial insemination treatments may be performed to correspond to appropriate times when the animal 108A is capable of conceiving. In some examples, the livestock management server 102 provides a prompt to the livestock technician user 114 indicating that a scheduled treatment activity is to be performed.

In some examples, the livestock technician user 114 observes the behavior, appearance, or other quality of the animal 108A and concludes that a treatment activity is warranted. For example, if the animal 108A is injured, appears sluggish, or is otherwise looking or behaving outside of a normal range, the livestock technician user 114 may determine that a treatment activity should be performed. In some examples, the livestock technician user 114 performs a diagnostic action to determine if a treatment activity should be performed. For example, the livestock technician user 114 may use a suitable thermometer to take the temperature of the animal 108A. If the temperature is high, indicating an infection, the livestock technician user 114 may perform a suitable treatment activity. In some examples, the livestock technician user 114 places the user computing device 104A in communication with the bolus 112A ingested by the animal 108A. As described herein, the bolus 112A may provide sensor data describing the animal 108A such as, for example, an internal temperature, an internal pH, a heart rate, etc. The sensor data from the bolus 112A may be used to determine whether a treatment activity should be performed.

The user computing device 104A and/or the livestock management server 102 may be programmed to execute a diagnostic routine. For example, the livestock management user 114 may input to the user computing device 104A (via the GUI 124) various data about the animal 108A including, for example, notes about the animal's appearance, the animal's temperature (manually taken and/or received from the bolus 112A), other sensor data from the bolus 112A, and the like. The user computing device 104A and/or the livestock management server 102 may be programmed to use this data about the animal 108A to select an appropriate treatment activity (if any).

Figure 2:
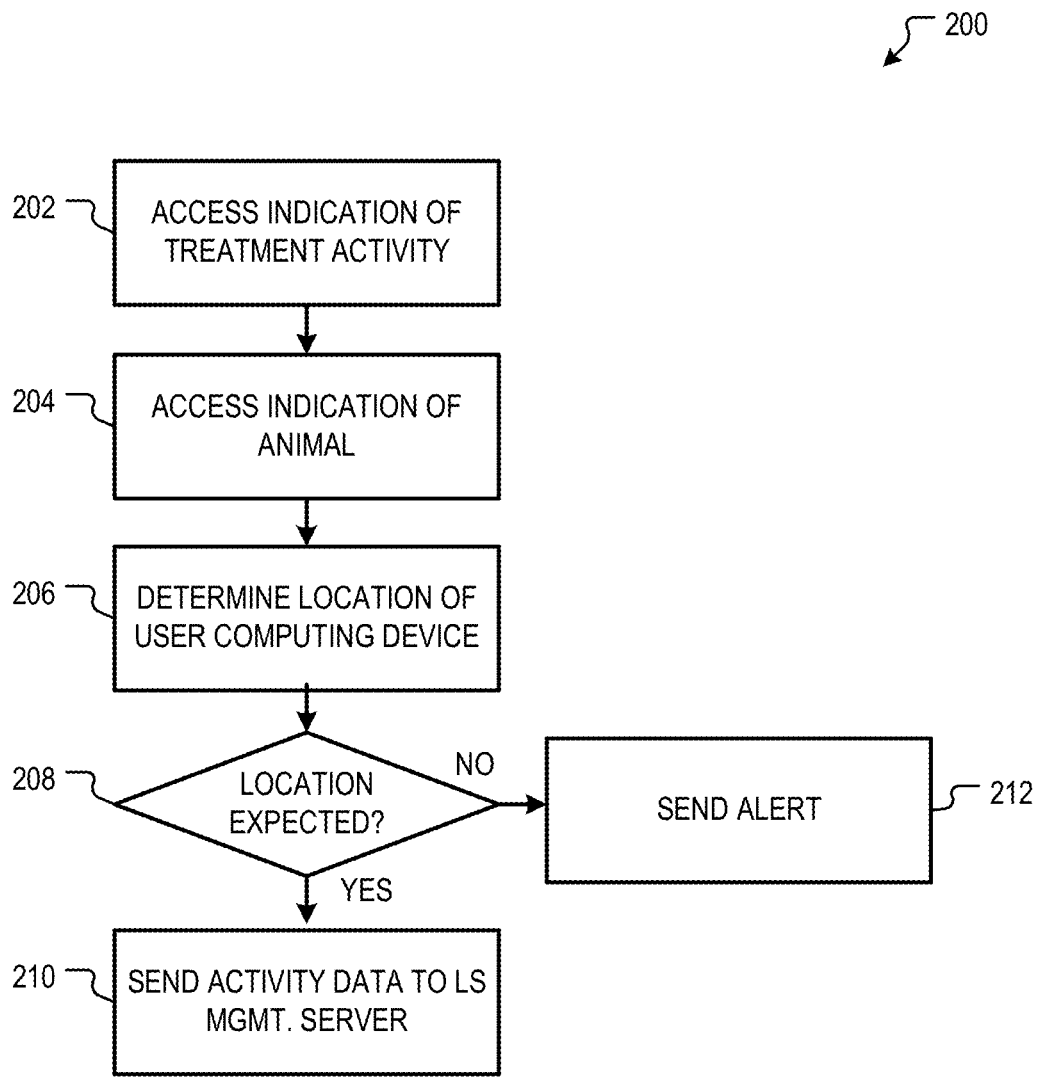
FIG. 2 is a flowchart showing one example of a process flow that may be executed by the user computing device in the example environment of FIG. 1 to manage animal treatment activities.

FIG. 2 is a flowchart showing one example of a process flow 200 that may be executed by the user computing device 104A of the livestock technician user 114 in the example environment of FIG. 1 to manage animal treatment activities. At operation 202, the user computing device 104A accesses an indication of a treatment activity to be performed by the livestock technician user 114. In some examples, the indication of the treatment activity is provided by the livestock technician user 114 via the GUI 124. In some examples, the indication of user activity can be generated by the user computing device 104A and/or by the livestock management server 102 (e.g., the treatment management service 126). For example, the user computing device 104A and/or livestock management server 102 may select a treatment activity for an animal based on information about the animal provided by the livestock technician user 114 via GUI 124 and/or from a bolus 112A, 112C or another sensor device.

At operation 204, the user computing device 104A accesses an indication of the animal 108A that is to be the subject of the treatment activity. In examples where the user computing device 104A determines the treatment activity, the indication of the animal 108A may be accessed from a memory of the user computing device 104A. In examples where the livestock management server 102 selects the treatment activity, the indication of the animal 108A may be received from the livestock management server 102. In some examples, the livestock technician user 114 enters the indication of the animal 108A via the GUI 124. For example, the livestock technician user 114 may read a serial number or other identifier of the animal 108A from the tag 110A or other location on the animal and enter the identifier via the GUI 124, for example, via the animal entry field 142. In some examples, the user computing device 104A receives the indication of the animal 108A via a wireless communication with an RFID tag 110A, bolus 112A or other suitable component that is coupled to and/or within the animal 108A.

At operation 206, the user computing device 104A determines its current location. This can be performed in any suitable manner. In some examples, the user computing device 104A utilizes a Global Navigation Satellite System (GNSS), such as a Global Positioning System (GPS) to determine its current location. In some examples, the user computing device 104A may utilize wireless triangulation or any other suitable locating technique in addition to or instead of a GNSS system.

At operation 208, the user computing device 104A determines if the current location of the user computing device 104A is within a threshold distance of an expected location of the animal 108A. The expected location of the animal 108A may be a location where the animal 108A is likely to be. For example, the expected location of the animal 108A may be a pen, feeding area, or other location at a farm, ranch, or similar facility where the animal 108A should be. The current location of user computing device 104A should be near the expected location of the animal 108A when the livestock technician user 114 performs the treatment activity. For example, if the treatment activity is being entered to the user computing device 104A when the livestock technician user 114 is not at or near the location of the animal 108A, it may indicate that the livestock technician user 114 is not actually performing the treatment activity and/or that the activity is being reported after it is performed, when errors may be more likely.

In some examples, the expected location of the animal 108A may vary by time. For example, the animal 108A may be expected to be at a feeding area during a feeding time and may be expected to be in a pasture at other times. In some examples, the user computing device 104A receives the expected location of the animal 108A from the livestock management server 102. In some examples, the expected location of the animal 108A is an actual location of the animal 108A measured by a bolus 112A, tag 110A, or other suitable device at the animal 108A that is capable of finding its own location via GNSS, wireless triangulation, and/or the like.

If the current location of the user computing device 104A is within a threshold distance of the expected location of the animal 108A, the user computing device 104A may, at operation 210, send data about the treatment activity to the livestock management server 102. The data sent to the livestock management server may include, for example, the indication of the animal 108A and an indication of the current location of the user computing device 104A. In some examples, the user computing device 104A also includes an indication of the treatment activity and/or an indication of the user computing device 104A or livestock technician user 114. The livestock management server 102 (e.g., the stamping service 128) may provide a timestamp for the received data and store it, for example, at the database 130 and/or at the livestock blockchain storage 134 via the blockchain API 132, for example, as described herein.

If the current location of the user computing device 104A is not within the threshold distance of the expected location of the animal 108A, as described herein, it may indicate that the data regarding the treatment activity is false and/or a less accurate after-the-fact recording. Accordingly, at operation 212, the user computing device 104A may send an alert message 135 indicating the reported treatment activity. In some examples, the alert message 135 may include the indication of the treatment activity, the indication of the animal 108A and an indication of the user computing device 104A and/or associated livestock technician user 114. The alert message 135 may be provided to the livestock management server 102 (e.g., the treatment management service 126 thereof). The livestock management server 102, in response, may send the alert message 136 to the user computing device 104B of the administrative user 116. The administrative user 116, for example, may investigate the reported treatment activity to determine whether the activity actually took place and whether it has been accurately reported.

In some examples, the livestock technician user 114 prompts the user computing device 104A to perform some or all of the operations of the process flow 200 by selecting an actuate element of the GUI 124, such as the save/submit button 144. For example, selecting the actuate element may prompt the user computing device 104A to determine its current location at operation 206 and proceed to operation 208 as described herein. In some examples, the determination of the current location of the user computing device 104A is not indicated at the GUI 124 and may not be known to the livestock technician user 114.

Also, in some examples, the livestock management server 102 compares the current location of the user computing device 104A to the expected location of the animal 108A. This may be in addition to or instead of performing the comparison at the user computing device 104A. If the livestock management server 102 compares current location of the user computing device 104A to the expected location of the animal 108A, it may determine to send the alert message 136 to the administrative user 116 (or not) based on its own comparison and/or based on the alert message 135 received from the user computing device 104A. It will be appreciated that in some examples where the comparison between the current location of the user computing device 104A and the expected location of animal is performed at the livestock management server 102, the operations 208 and 212 of the process flow 200 may be omitted.

Figure 3:
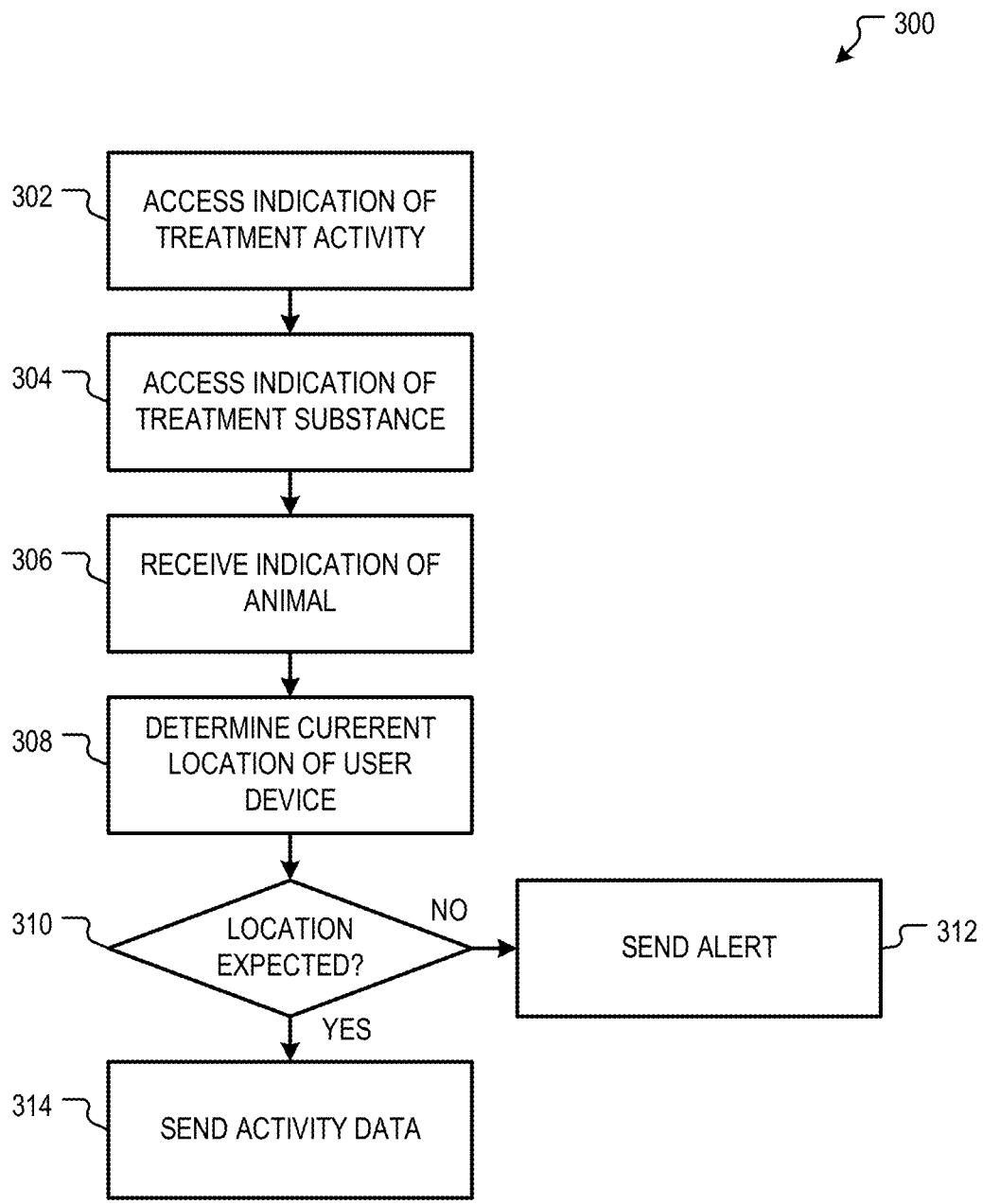
FIG. 3 is a flowchart showing one example of a process flow that may be executed by the user computing device of the livestock technician user in the example environment of FIG. 1 to manage animal treatment activities that include providing a treatment substance to the animal.

FIG. 3 is a flowchart showing one example of a process flow 300 that may be executed by the user computing device 104A of the livestock technician user 114 in the example environment of FIG. 1 to manage animal treatment activities that include providing a treatment substance to the animal. At operation 302, the user computing device 104A accesses an indication of a treatment activity to be performed by the livestock technician user 114. The indication may be provided by the livestock technician user 114 via the GUI 124, determined by the user computing device 104A and/or received from the livestock management server 102 (e.g., the treatment management service 126 thereof).

At operation 304, the user computing device 104A accesses an indication of the treatment substance to be provided during the treatment activity. The indication of the treatment substance may include an identity of the treatment substance and, in some examples includes additional information such as, for example, a dosage of the treatment substance to be provided, a container (e.g., bottle or vial) from which the dose of treatment substance is taken, and the like. In some examples, the livestock technician user 114 provides the indication of the treatment substance via the GUI 124. For example, the livestock technician user 114 may enter the indication via a treatment substance entry field 143 of the GUI 124.

In some examples, the user computing device 104A determines some or all of the indication of the treatment substance by interactions with a treatment substance container 118. For example, as described herein, the livestock technician user 114 may be prompted via the GUI 124 to capture an image of a graphical code 122 on the treatment substance container 118. In some examples, the user computing device 104A opens a short-range wireless communication session with a wireless communication circuit 120 of the treatment substance container 118. The treatment substance container 118 provides the indication of the treatment substance via the wireless communication channel.

At operation 306, the user computing device 104A accesses an indication of the animal 108A that is to be the subject of the treatment activity. In examples where the user computing device 104A determines the treatment activity, the indication of the animal 108A may be accessed from a memory of the user computing device 104A. In examples where the livestock management server 102 selects the treatment activity, the indication of the animal 108A may be received from the livestock management server 102. In some examples, the livestock technician user 114 enters the indication of the animal 108A via the GUI 124, as described herein.

At operation 308, the user computing device 104A determines its current location. For example, the operation 308 may be prompted when the livestock technician user 114 selects the save/submit button 144 or another actual element at the GUI 124. At operation 310, the user computing device 104A determines if the current location of the user computing device 104A is within a threshold distance of an expected location of the animal 108A. If the current location of the user computing device 104A is within a threshold distance of the expected location of the animal 108A, the user computing device 104A may, at operation 314, send data about the treatment activity to the livestock management server 102.

If the current location of the user computing device 104A is not within the threshold distance of the expected location of the animal 108A, as described herein, the user computing device 104A may, at operation 314, send an alert message 135 indicating the reported treatment activity and/or treatment substance. In some examples, the alert message 135 may include the indication of the treatment activity, the indication of the treatment substance, the indication of the animal 108A and an indication of the user computing device 104A and/or associated livestock technician user 114. The alert message 135 may be provided to the livestock management server 102 (e.g., the treatment management service 126 thereof). The livestock management server 102, in response, may send the alert message 136 to the user computing device 104B of the administrative user 116. The administrative user 116, for example, may investigate the reported treatment activity to determine whether the activity actually took place and whether it has been accurately reported. For example, the alert message 136 may include record data describing the treatment activity including, for example, the indication of the animal 108A, the indication of the treatment substance as well as the current location of the user computing device and, in some examples, the expected location of the animal 108A.

As described herein, there are some examples in which the livestock management server 102 compares the current location of the user computing device 104A to the expected location of the animal 108A. In some of these examples, the operations 310 and 312 may be omitted.

Figure 4:
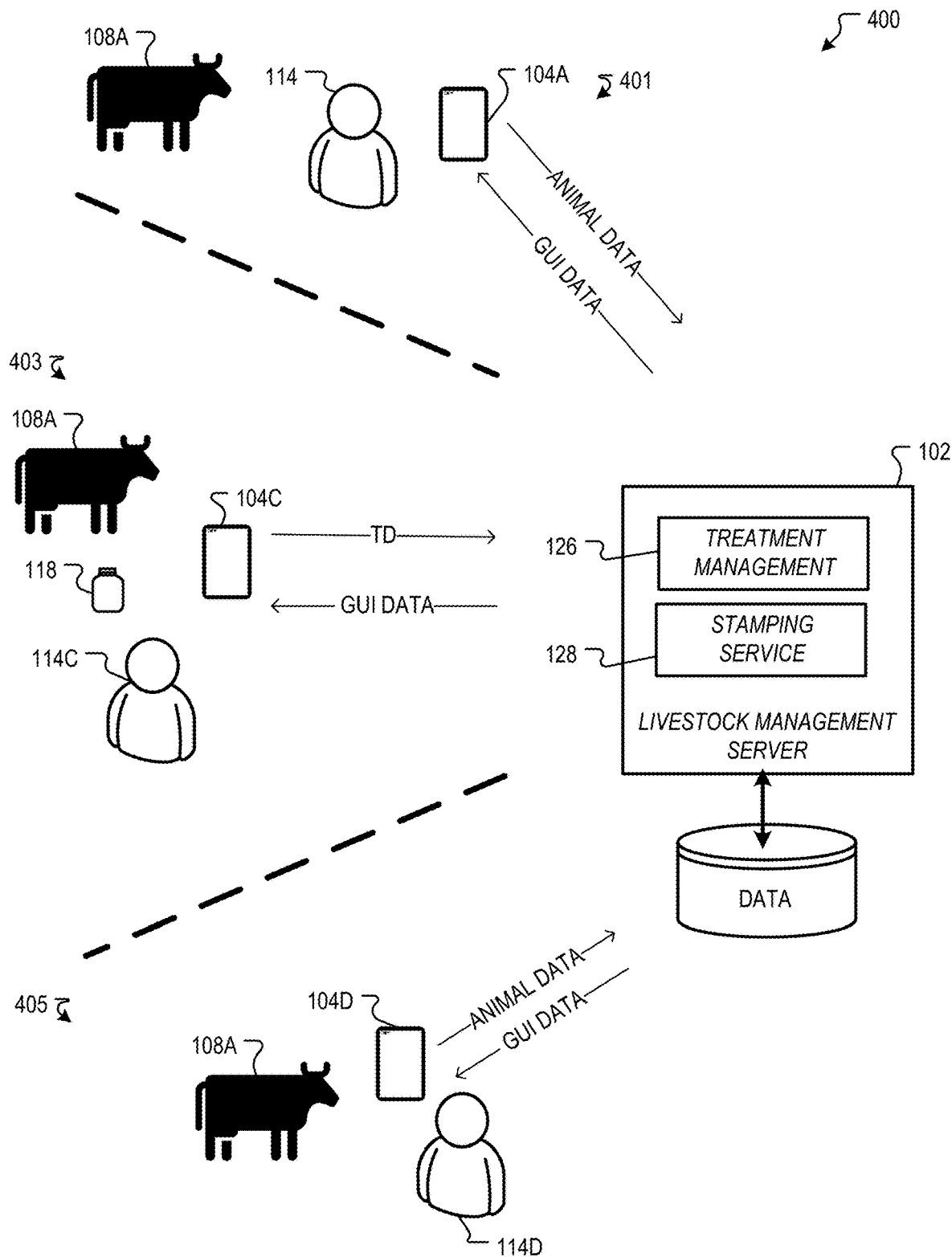
FIG. 4 is a diagram showing a workflow illustrating that treatment activities for a single animal can be performed by different livestock technician users.

FIG. 4 is a diagram showing a workflow 400 illustrating that treatment activities for a single animal 108A can be performed by different livestock technician users 114, 114C, 114D. In this example, the livestock technician user 114 performs a treatment activity 401 using the user computing device 104A; the livestock technician 114C performs a treatment activity 403 using a user computing device 104C and livestock technician user 114D performs a treatment activity 405 using a user computing device 104D. The user computing devices 104C, 104D may be similar to the user computing devices 104A, 104B described herein.

In the example of FIG. 4, the treatment activity 401 involves gathering data about the animal 108A. For example, the livestock technician user 114 may record observation data bout the animal via the GUI 124 and/or may use a sensor, such as a thermometer, to gather data about the animal 108A. In some examples, the treatment activity 401 includes the livestock technician user 114 using the user computing device 104A to read data from a bolus 112A (not shown in FIG. 4) associated with the animal 108A. The animal data may be provided to the livestock management server 102 where the stamping service 128 may timestamp the received animal data and store it at the livestock blockchain storage 134 and/or database 130, as described herein. In some examples, the treatment activity 401 may be handled by the user computing device 104A in a manner as described herein with respect to the process flow 200 of FIG. 2 and/or according to the process flow 500 of FIGS. 5 and 6.

The treatment activity 403 involves providing a treatment substance to the animal 108A. For example, the user computing device 104A and/or the livestock management server 102 (e.g., the treatment management service 126 thereof) may use the animal data received from the treatment activity 401 and/or other data about the animal 108A to determine that the treatment substance should be provided to the animal 108A at the treatment activity 403 and/or a dose of the treatment substance. The livestock technician user 114C may be requested to perform the treatment activity 403, for example, via the GUI 124 provided at the user computing device 104C. For example, the livestock management server 102 (e.g., the treatment management service 126 thereof) may send to the user computing device 104C a request to perform the treatment activity 403. The user computing device 104C, in some examples, manages the treatment activity 403 as described herein with respect to the process flow 300 of FIG. 3 and/or according to the process flow 500 of FIGS. 5 and 6.

The treatment activity 405 involves gathering additional animal data, for example, as a follow up to the providing of the treatment substance at the treatment activity 403. The livestock technician user 114D may be requested to perform the treatment activity 405, for example, via the GUI 124 provided at the user computing device 104D. For example, the livestock management server 102 (e.g., the treatment management service 126 thereof) may send to the user computing device 104D a request to perform the treatment activity 405. In some examples, the treatment activity 405 may be handled by the user computing device 104A in a manner as described herein with respect to the process flow 200 of FIG. 2 and/or according to the process flow 500 of FIGS. 5 and 6.

Figure 5:
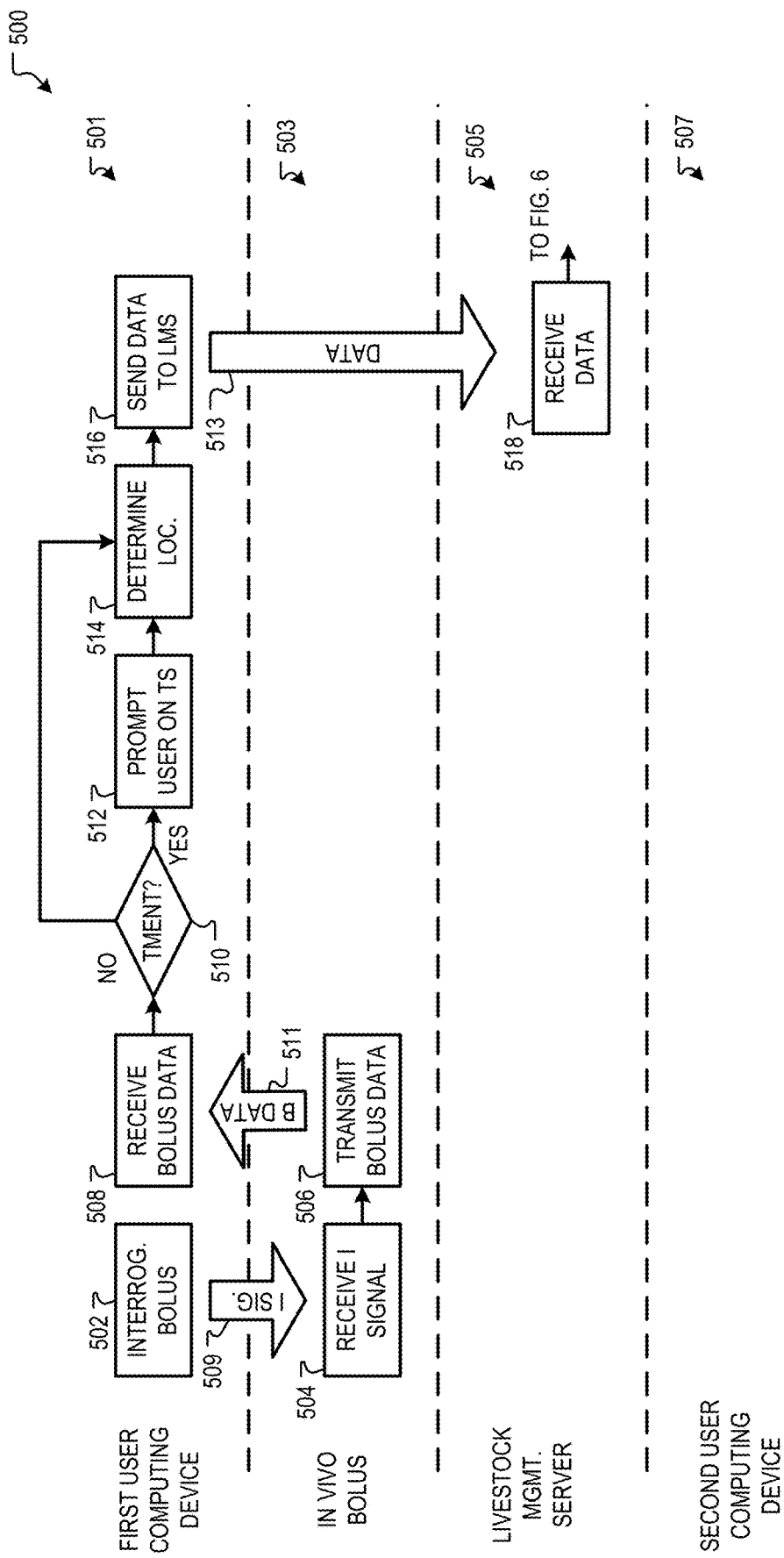
FIGS. 5 and 6 are a flowchart showing one example of a process flow that may be executed in the environment of FIG. 1 to manage treatment activities provided to an animal.
Figure 6:
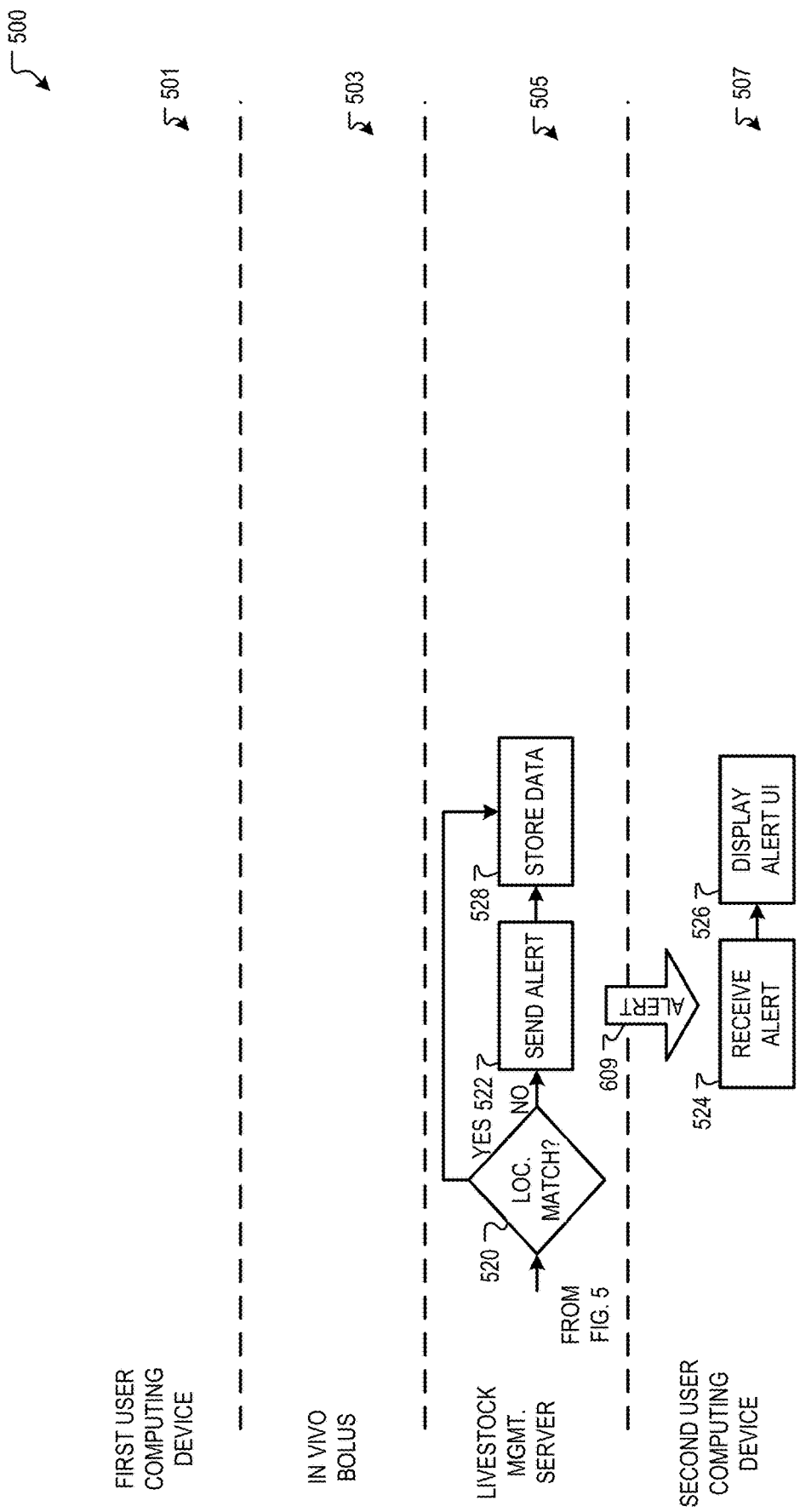

FIGS. 5 and 6 are a flowchart showing one example of a process flow 500 that may be executed in the environment 100 of FIG. 1 to manage treatment activities provided to an animal. FIGS. 5 and 6 include four rows 501, 503, 505, 507. The row 501 includes operations that may be performed by a first user computing device of a livestock technician, such as the user computing device 104A of the livestock technician user 114. The row 503 includes operations that may be performed by an in vivo bolus, such as the bolus 112A or the bolus 112C. The row 505 includes operations that may be performed by the livestock management server 102. The row 507 includes operations that may be performed by a second user computing device of an administrative user, such as the user computing device 104B of the administrative user 116.

At operation 502, the first user computing device interrogates the in vivo bolus at operation 502 by sending an interrogation signal 509. This may be performed directly by the first user computing device (e.g., in examples where the first user computing device has an integrated RFID reader and/or where the bolus communicates using another short-range wireless communication medium). In other examples, the first user computing device interrogates the bolus using an external RFID reader (not shown in FIG. 5).

The bolus receives the interrogation signal 509 at operation 504. In response to the interrogation signal 509, the bolus transmits bolus data 511 to the first user computing device at operation 506. The bolus data 511 can include an identifier of the animal and may, in some examples, also include sensor data captured by one or more sensors on the bolus. The first user computing device receives the bolus data at operation 508.

At operation 510, the first user computing device determines if a treatment substance should be administered to the animal based on the bolus data. For example, if the bolus data indicates that the animal is running a fever or otherwise provides an indication that the animal is ill, the first user computing device may determine that a treatment substance should be administered. In some examples, the first user computing device provides the bolus data to the livestock management server, which may determine, using the bolus data and/or other data about the animal, that a treatments substance should be administered.

If the first user computing device (or the livestock management server) determines that a treatment substance should be administered, the first user computing device prompts the livestock technician to provide the treatment substance at operation 512. For example, the prompt may be provided via the GUI provided at the first user computing device. The livestock technician may administer the treatment substance in response to the prompt.

The livestock technician user may provide an indication to the first user computing device when the treatment substance is administered. For example, the livestock technician user may select an actuation element, such as a save/submit button, on the GUI provided by the first user device. In response, the first user computing device may determine its current location at operation 514 and send data to the livestock server at operation 516.

If no treatment substance is to be administered, the first user computing device may determine its current location at operation 514. For example, after receiving the bolus data, the livestock technician user may select the actuation element at the GUI, prompting the first user computing device to determine its location at operation 514.

After determining its current location, the first user computing device sends data 513 to the livestock management server at operation 516. The livestock management server 102 receives the data at operation 518. The data may include, for example, an indication of the animal (e.g., provided by the bolus and/or entered by a user), an indication of any sensor data provided by the bolus. If a treatment substance was provided to the animal, the data may include an indication of the treatment substance including, for example, an identifier of the treatment substance received from a container including the treatment substance, a dose of the treatment substance administered, and/or the like.

Referring to FIG. 6, at operation 520, the livestock management server determines whether the current location of the first user computing device received from the first user computing device is within a threshold distance of an expected location of the animal. If the current location of the first user computing device is not within the threshold distance of the expected location of the animal, the livestock management server, at operation 522, sends an alert message (e.g., alert message 136) to the second user computing device. The second user computing device receives the alert message at operation 524 and, at operation 526, may display the alert message (e.g., to an administrative user) at a GUI provided at a display or other output device of the second user computing device.

If the current location of the first user computing device is within the threshold distance of the animal's expected location, or in addition to sending the alert at operation 522, the livestock management server may store the data received from the first user computing device at operation 528. This may include storing the data at a record associated with the animal at a database, such as the database 130 of FIG. 1. In some examples, the data may be stored at a blockchain storage, such as the livestock blockchain storage 134 of FIG. 1. For example, the livestock management server 102 may be in communication with a block application programming interface (API), such as the blockchain API 132 of FIG. 1. The livestock management server may provide the data to the blockchain API. The blockchain API may generate a data block from the received data. Generating the data block may include, for example, generating appropriate cryptographic representations of the data and/or of data stored at a previous data block of the block chain. The blockchain API may also add the data block as a new record at the blockchain storage.

Figure 7:
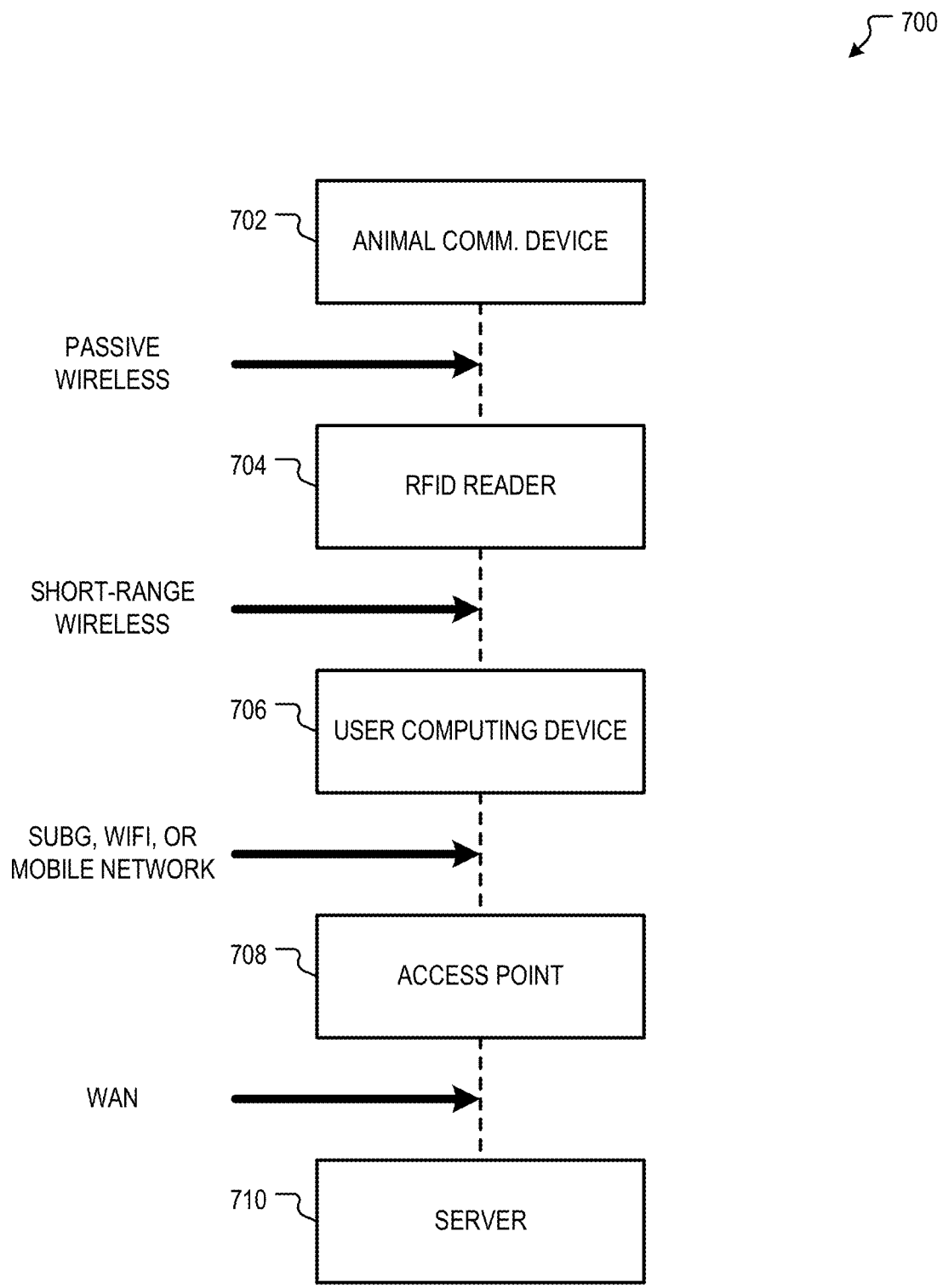
FIG. 7 is a diagram illustrating communication connections between an animal communication device and the livestock management server.

FIG. 7 is a diagram 700 illustrating communication connections between an animal communication device 702 and a livestock management server 710. The animal communication device 702 may be, for example, a bolus, such as the example boluses 112A, 112C, an RFID tag such as the example tags 110A, 110B, 110C, 110D. The animal communication device 702 is in communication with an RFID reader 704 via a passive wireless connection, such as RFID. For example, the RFID reader 704 may illuminate the animal communication device 702 with an electromagnetic signal, causing the animal communication device 702 to transmit a response signal including data from the animal, for example, an animal identifier, sensor date from the animal, and the like.

In the example of FIG. 7, the RFID reader 704 is in communication with the user computing device 706 via a short-range wireless communication medium such as RFID, NFC, Bluetooth®, and/or the like. In some examples, the RFID reader 704 is integral to the user computing device 706 and, in some examples, may be in communication with the user computing device 706 via a wired universal serial bus (USB) or other suitable wired connection. The RFID reader 704 may provide the user computing device 706 with data received from the animal communication device 702.

The user computing device 706 may be used by a livestock technician user, such as the user computing device 104A used by the livestock technician user 114 of FIG. 1. The user computing device 706 may be in communication with the livestock management server 710 via an access point 708, which may be, for example, a mobile communication tower, a wireless access point, or any other suitable network component. The user computing device 706 may be in communication with the access point 708 vi, for example, a subg connection (e.g., a connection with a carrier frequency of less than 1 GHz), a WiFi connection, a mobile/cellular connection or other suitable connection. The access point 708 may be in communication with the livestock management server 710 via a wide area network (WAN). The user computing device 705 may communicate data to the livestock management server 710 via the access point 708 including, for example, data received from the animal communication device, data determined by the user computing device 706, such as a current location, and/or data received from a user via a GUI as described herein.

Figure 8:
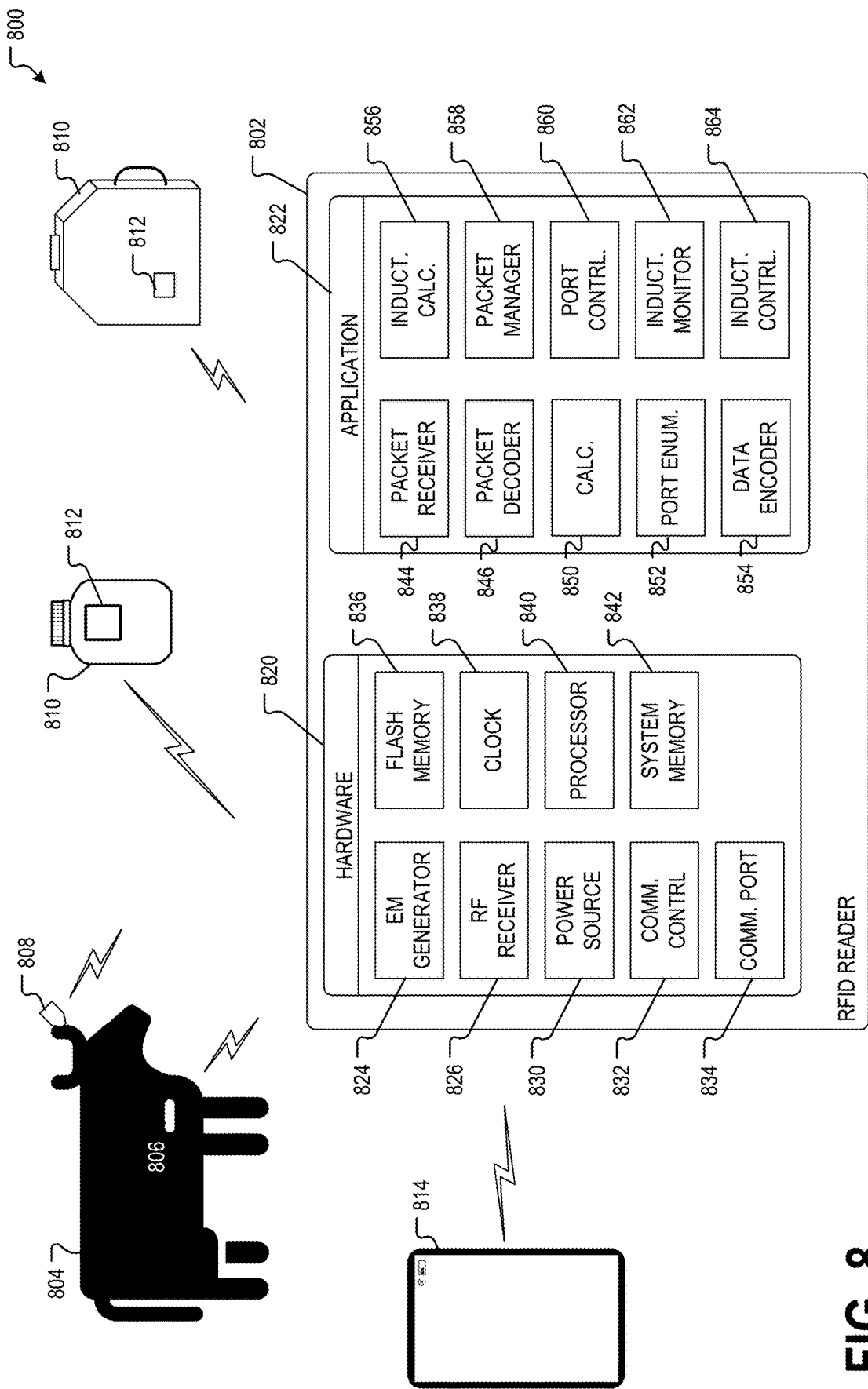
FIG. 8 is a diagram of an environment including an RFID reader in communication with various RFID devices.

FIG. 8 is a diagram of an environment 800 including an RFID reader 802 in communication with various RFID devices. In some examples, the RFID reader 802 is a component of a user computing device. In other examples, the RFID reader 802 is in communication with a user computing device 814 via a wired or wireless connection. The RFID reader 802 may be configured to wirelessly communicate with various RFID devices. For example, a bolus 806 ingested by an animal 804 may provide sensor data to the RFID reader 802, as described herein. An RFID device 808 on the animal 804 may provide animal identifier data. An RFID device 812 on a treatment substance container 810 may provide data about the treatment substance stored at the treatment substance container 810, as described herein.

Referring now to the RFID reader 802 may transmit a radio-frequency carrier signal to one or more of the RFID devices 806, 808, 812 (or another RFID device as described herein. The RFID may respond to the radio-frequency carrier signal with a RFID data signal to send and receive an amount of RFID information from the RFID device.

The RFID reader 802 may include hardware 820 and an RFID reader application 822, which may be stored in a memory of the RFID reader 802 as firmware. The hardware 820 may include a processor 840 and system memory 842. The hardware 820 may also include an electromagnetic field generator 824 which comprises an electromagnetic drive antenna for transmitting radio frequency signals. The electromagnetic field generator 824 manages the power level and induction of the electromagnetic drive antenna. In various examples, the electromagnetic drive antenna has an inductance between about 3.5 H and about 4.5 H with a 1-to-4 twist. The hardware 820 may also include a radio frequency signal receiver 826 including a receiving antenna. The radio frequency signal receiver manages the receiving antenna, which collects the RFID information sent by the various RFID devices 806, 808, 812. In another example, the EM generator 824 and radio frequency receiver are consolidated into a single component using a common antenna.

Figure 9:
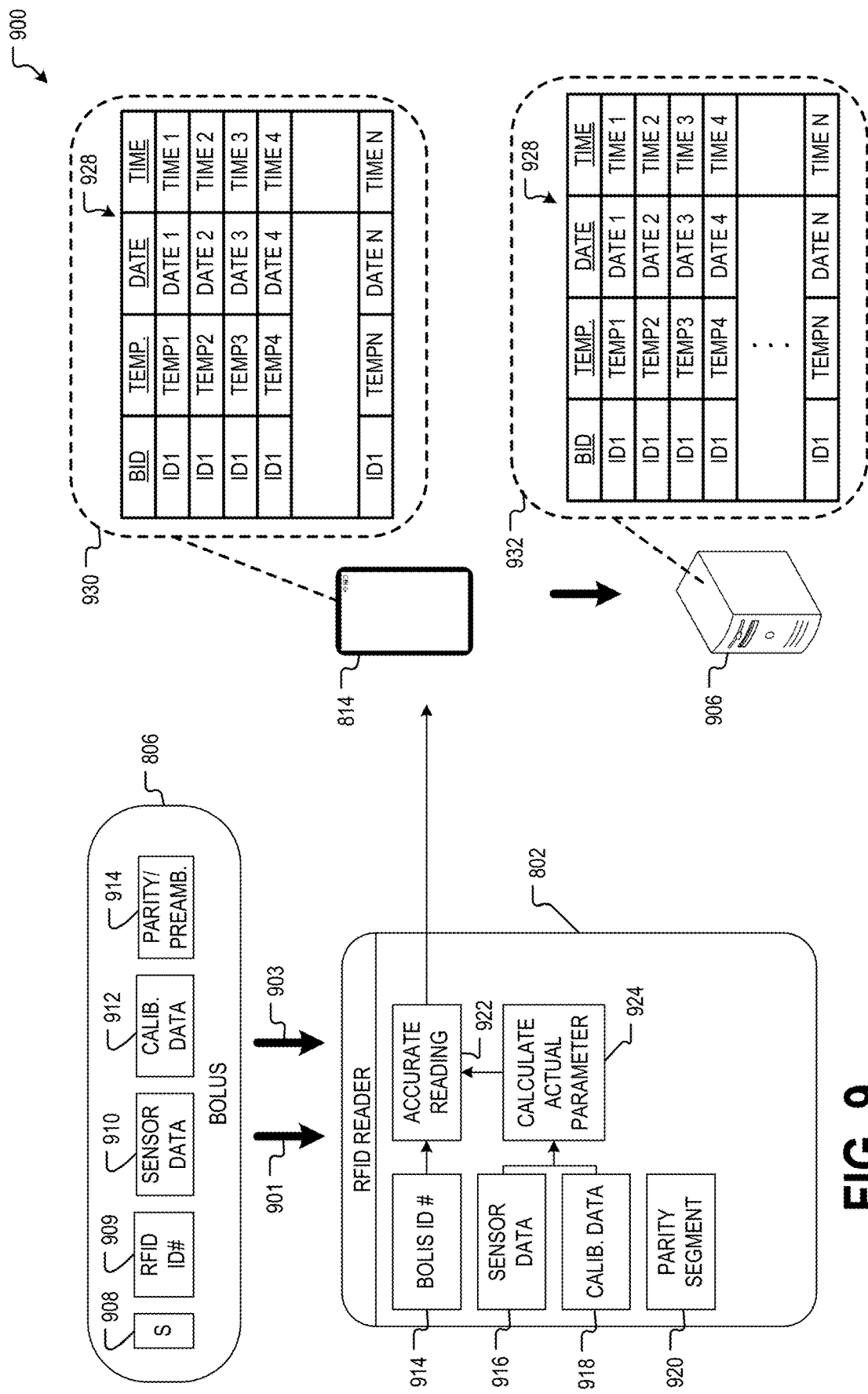
FIG. 9 is a workflow diagram showing one example of RFID data being transferred from an RFID device to the livestock management server via the user computing device.

The RFID reader hardware 820, can further include a RFID reader processor 840 which can perform computations based on RFID information 901 and calibration data 903 of FIG. 9 received from the various RFID devices 806, 808, 812. A first RFID reader memory 836 can store the amount of RFID information 901 transmitted from the RFID devices 806, 808, 812. In an alternative the RFID reader processor 840 can integrally include the first RFID reader memory 836. A second RFID reader memory 842 used by the RFID reader processor 840 can perform read-write functions.

The hardware 820 can further include a communication controller 832 which provides communication with the livestock management server 906 of FIG. 9 and/or user computing device 814 via a local area network (LAN) or WAN; a LAN port or a WAN port 834 for wired or wireless connection to the livestock management server 906 and/or user computing device 814. In alternate embodiment the RFID reader processor 840 can be programmed to further provide the functionalities of the communication controller 832.

A clock 838 can function to govern timing of events controlled by the RFID reader processor 840 and may couple a date-time stamp to the amount of RFID information 901. A RFID reader power source 830 may include a voltage regulator to provide, for example, a potential of 12 volts and a direct current in the range of 3.5-4.5 amperes.

The RFID reader application 822 The RFID reader 802 may include modules which can be stored in the first RFID reader memory 836 of the RFID reader 802 (or could be located in the livestock management server 906 or in the user computing device 814). The RFID reader application 822 stored and implemented by the hardware described herein can include an electromagnetic induction monitor module 862 which functions to monitor current inductance levels in the electromagnetic drive antenna. An electromagnetic inductance calculator module 856 may function to compare current electromagnetic inductance levels to a target electromagnetic inductance level. An electromagnetic inductance controller 864 may function to adjust current electromagnetic inductance level toward the target electromagnetic inductance level.

A packet receiver module 844 receives the RFID data signal transmitted with the radio-frequency carrier signal from the RFID devices 806, 808, 812. The packet receiver module 844 can be activated by detection of movement of an RFID device 806, 808, 812 in the electromagnetic field generated by the electromagnetic field generator 824. The packet receiver module 844 transfers the RFID data signal which can be decoded by a decoder module 846. The decoder module 846 can be activated by the packet receiver module 844 and can further function to separate RFID information 901 from a plurality of bit segments 908, 909, 910, 914 of FIG. 9 received from an RFID device 806, 808, 812. The decoder module 846 can, as to certain RFID information 901, activate a RFID reader calculator module 850 to perform calculation functions and generate RFID object characteristic values 922 of FIG. 9 from sensor data 916 of FIG. 9. A data encoder module 854 may function to assemble transmitted RFID information 901 of the bit segments 908, 909, 910, 914 received from an RFID device 806, 808, 812. The data encoder module 854 may also transfer data packets output from the RFID reader data encoder module 854. A serial packet manager 858 may handle data packets output from the data encoder module 854 to the communication port 834 for LAN or WAN transmission. A communication port enumerator module 852 functions to assign communication port information for a port controller module 860 which functions to control communications between the RFID reader 802 and the livestock management server 906 and/or the user computing device 814.

FIG. 9 is a workflow diagram 900 showing one example of RFID data being transferred from an RFID device (in this example the bolus 806) to the livestock management server 906 via the user computing device 814. In this example, the bolus 806 includes a RFID circuit, for example, located in a hollow inside the bolus 806. The RFID circuit comprises a first bit segment that can be encoded or re-encoded with an amount of RFID object identification information 909 (which can be a bolus identification number, animal identifier, and/or the like). A second bit segment of the RFID circuit can be encoded or re-encoded from time to time with sensed RFID object characteristics 910 received from a sensor at the bolus 806, such as a temperature sensor. Other sensed characteristics may include, for example, location, temperature, pH, heart rate, blood pressure, partial pressures of dissolved gases, or the like. Variation of the sensed RFID object characteristic(s) 910 can be continuously or intermittently updated by encoding or re-encoding the second bit segment 910 of the RFID circuit. A third bit segment of the RFID circuit can be encoded or re-encoded from time to time with an amount of calibration data 912 which allows a RFID object characteristic value 922 to be calculated from the sensed RFID object characteristic 910.

The RFID object identification information 909, the sensed RFID object characteristics 910, and the amount of calibration data 912 can be collected from the corresponding bit segments of the RFID circuit by the RFID reader 802 when the RFID object, in this example, the bolus 806, passes within sufficiently close proximity of the RFID reader 802. As to certain examples of the RFID reader 802 the RFID object identification information 909 and the sensed RFID object characteristics 910 and the calibration data 912 can be received by the RFID reader 802 and coupled to a time-date stamp 928 (which for example can take the form of HH:MM:SS and MM/DD/YY). An actual parameter 924 is determined from the sensor data 916 and the calibration data 918. The RFID object characteristic value 922 can be calculated by operation of a RFID reader calculator module 850 having a location in the RFID reader 802 or in the livestock management server 906 or the user computing device 814 (as to certain embodiments) using the sensed RFID object characteristic and the calibration data 912. A parity segment 920 can be located at the beginning and the end of the RFID information 901 from a plurality of bit segments 908, 909,910, 912, 914 to identify the start and the stop of the RFID information 901.

The RFID object identification information 909 and the sensed RFID object characteristics value 922 can be separated, sorted, and loaded into a current reads database table 930 stored in the user computing device 814. The user computing device 814 may provide the values stored at the current reads database table 930 to the livestock management server 906, where they may be stored for later use at a database table 932 of a datastore, such as the database 130 and/or livestock blockchain storage 134 of FIG. 1, as described herein.

FIGS. 10-15 are screen shots showing various screens that may be displayed at a user computing device as part of the GUI described herein.

Figure 10:
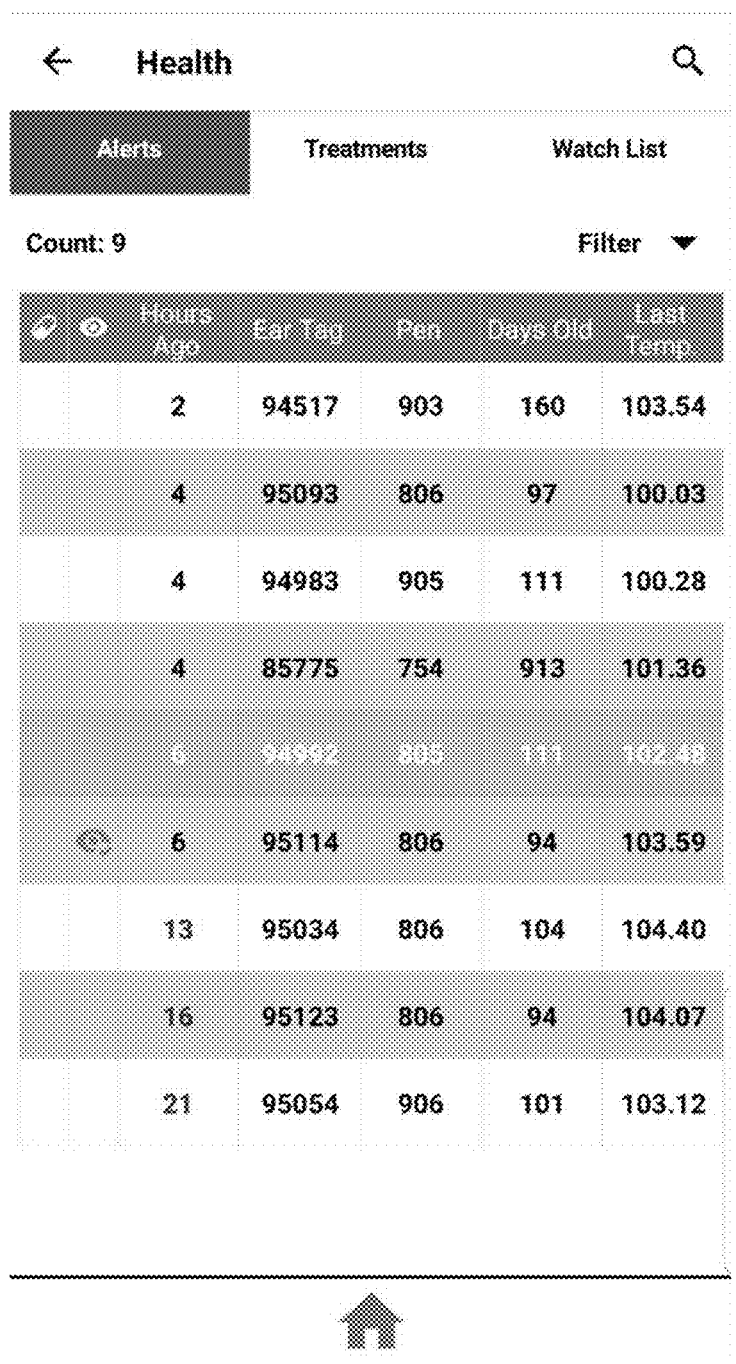

FIG. 10 shows one example of a screen 1000 that may be displayed to the livestock technician user 114 via the GUI 124 to indicate information about animals, such as animals 108A, 108B, 108C, 108D, 108E, 108F that may be the subject of a treatment activity and/or may receive a treatment substance. In the example of FIG. 10, the screen 1000 includes rows with each row corresponding to an animal. The row may include various records about an animal including a time since the animal was last examined, an animal identifier (e.g., an ear tag number), a pen where the animal is located, an age of the animal, a last animal temperature measured manually and/or by a bolus.

Figure 11:
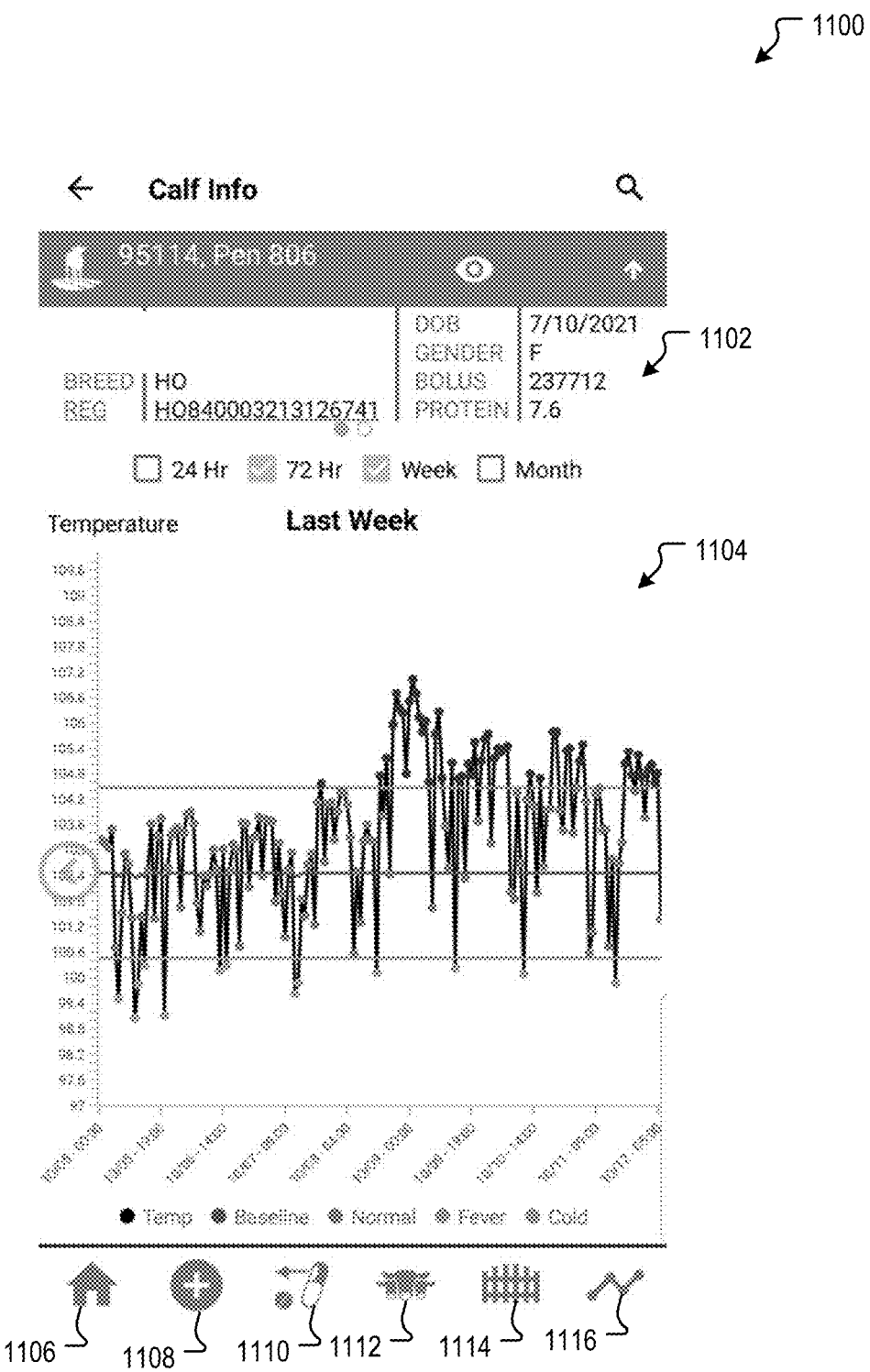

FIG. 11 shows one example screen 1100 that may be displayed to the livestock technician user 114 via the GUI 124 to indicate information about a particular animal. For example, the user computing device 104A may provide the screen 1100 when the user selects a row from the screen 1000. The screen 1100 may include information about the animal corresponding to the selected row.

In the example of FIG. 11, the screen 1100 includes an animal information field 1102 and a graph field 1104. The animal information field 1102 shows various data about the animal including, for example, breed and/or other genetic information; a date of birth, a gender, a bolus identifier and test results, such as a total protein reading for the animal. The graph field 1104 has a horizontal axis showing time and a vertical axis showing animal temperature. Points on the graph indicate temperature readings taken manually and/or via a bolus over. In the example of FIG. 11, the screen 1100 includes fields for selecting a range of time displayed on the horizontal axis. The points may be color-coded to indicate whether the corresponding temperature is within a baseline range, within a normal range, within a range indicating that the animal is cold, within a range indicating that the animal has a fever, and the like. The livestock technician user 114 may use data provided by the screen 1100 to determine whether the animal should receive a treatment activity, such as the administering of a treatment substance.

The example screen 1100 also includes UI elements 1106, 1108, 1110, 1112, 1114, 1116 that may be selected by the livestock technician user to access additional functionality of the user computing device 104A. A home button 1106 may be selected to return to a home screen. A plus button 1108 may be selected to provide information about a new animal. A treatment activity button 1110 may be selected to initiate at treatment activity for the animal. A return button 1112 may be selected to return to the screen 1000 of FIG. 10. A pen button 1114 may be selected to move the animal to a different pen. A data button 1116 may be selected to cause the user computing device 104A to display additional data about the animal.

Figure 12:
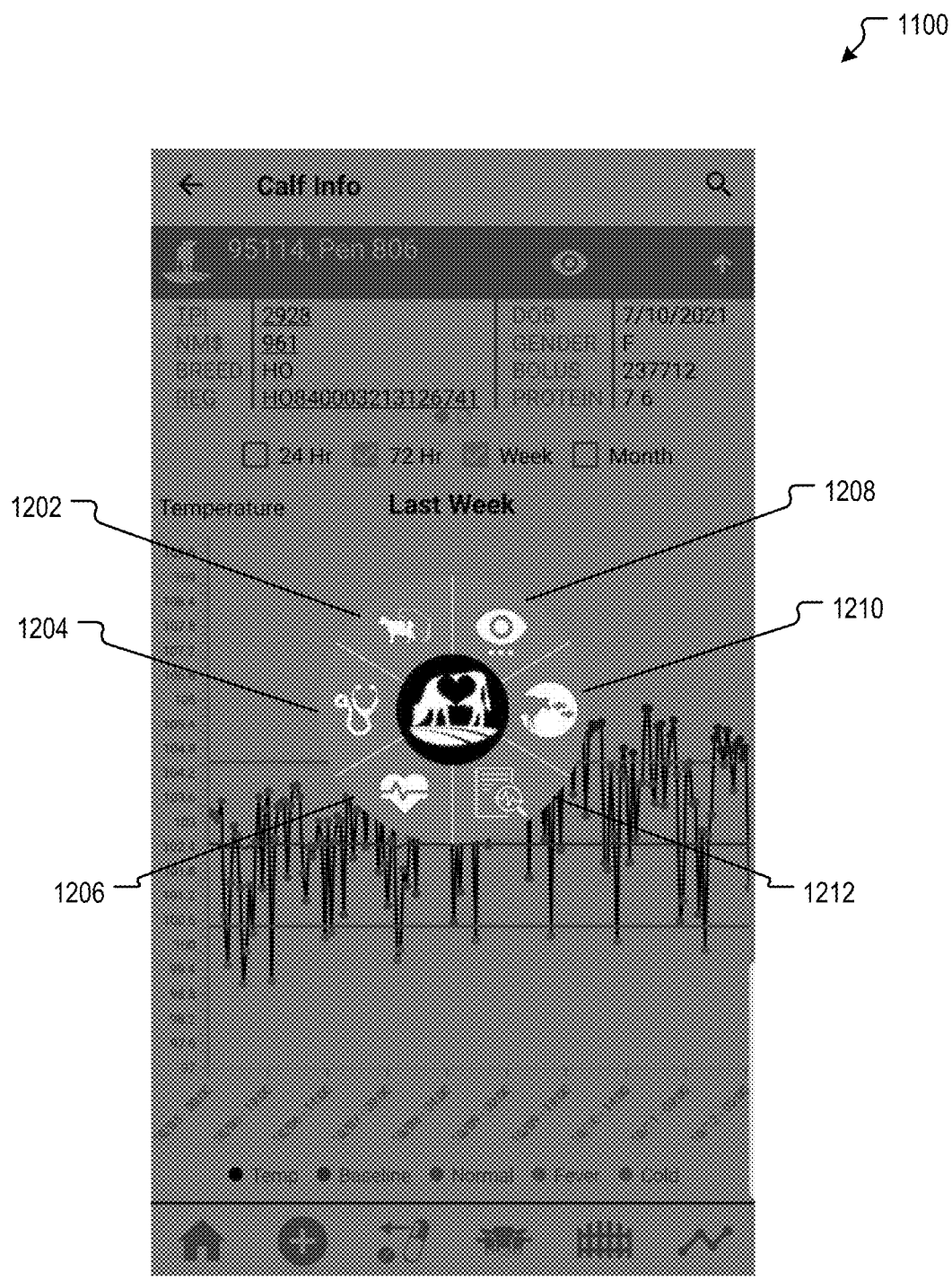

FIG. 12 shows another example of the screen 1100 of FIG. 11 after the livestock technician user has selected the treatment activity button. The screen 1100 includes additional input elements 1202, 1204, 1206, 1208, 1210, 1212. Input element 1202 may be selected by the livestock technician user to initiate an additional UI screen including an entry field for receiving information when a treatment substance associated with artificial insemination is provided to the animal. The input element 1204 may be selected by the livestock technician user to initiate an additional UI screen including one or more entry fields for receiving information about an animal's heart rate manually measured by the livestock technician user. Input element 1206 may be selected by the livestock technician user to initiate an additional UI screen including one or more entry fields for receiving data describing animal records. Input element 1210 may be selected by the livestock technician user to initiate an additional UI screen including one or more entry fields for receiving data regarding the provision of an ingestible treatment substance. Input element 1208 may be selected by the livestock technician user to initiate an additional UI screen including one or more entry fields for receiving data a treatment activity involving observation of the animal.

Figure 13:
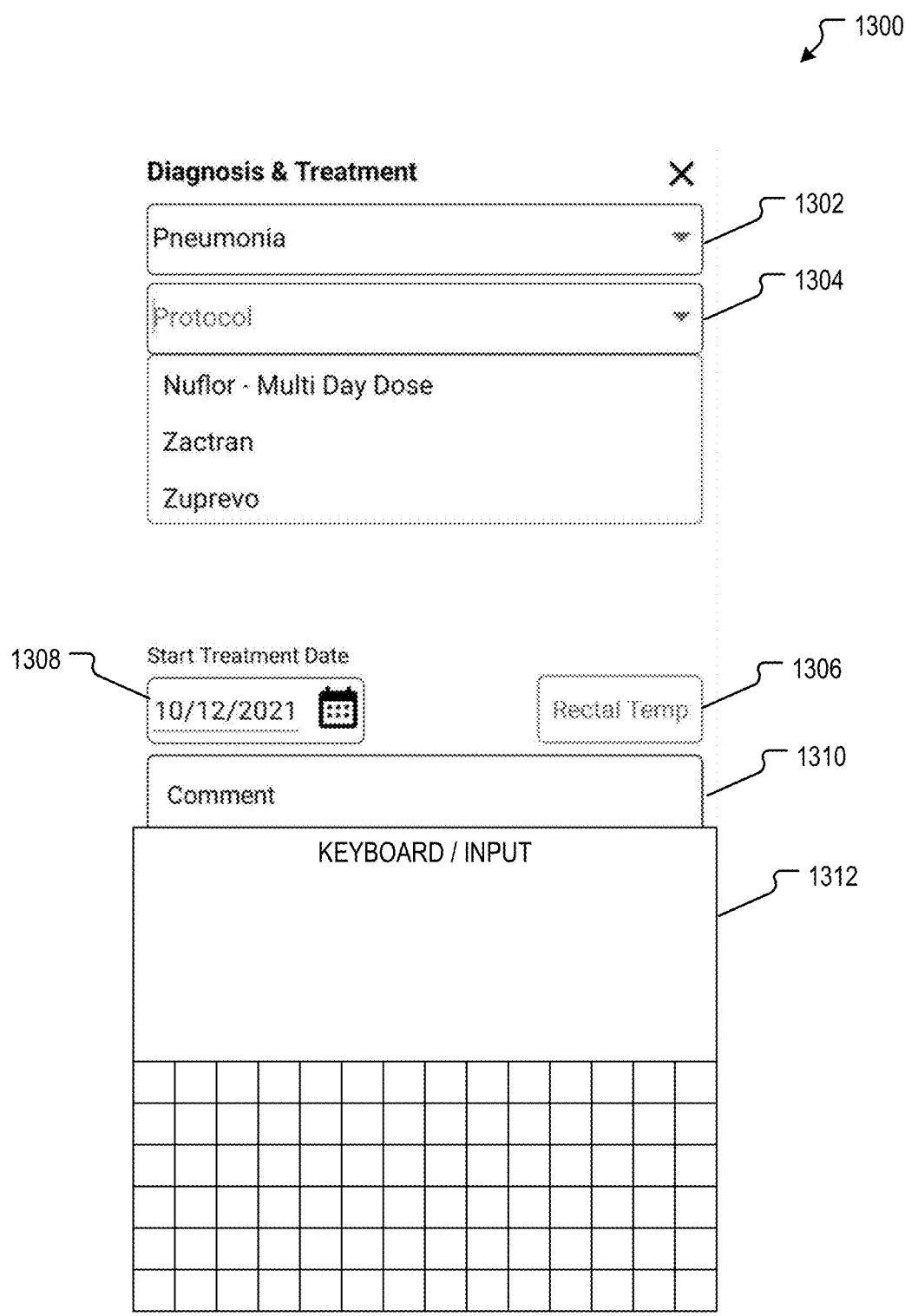

FIG. 13 shows a screen 1300 that may be displayed at the GUI 124, for example, when the livestock technician user is to provide a treatment substance that includes a medication for an animal condition, such as an illness. For example, the screen 1300 may be displayed upon selection of one of the input elements 1202, 1204, 1206, 1208, 1210, 1212 of FIG. 12. Ata diagnosis input field 1302, the livestock technician user may enter a diagnosis for the animal. At a treatment substance entry field 1304, the livestock technician user may enter a treatment substance to be provided to the animal. The treatment substance may be provided once, or over a course of treatment. For example, the livestock management server may prompt the livestock technician user to provide additional doses of the treatment substance at appropriate times.

A start treatment date entry field 1308 may be for the livestock technician user to enter a time when the first dose of the treatment substance is provided to the animal. A rectal temperature entry field 1306 may be for receiving a rectal temperature of the animal taken by the livestock technician user. A comment entry field 1310 may be for receiving additional comments provided by the livestock technician user. A keyboard/input field 1312 may include keys on a touchscreen. The keyboard/input field 1312 may be used by the livestock technician user to fill out the various entry fields 1302, 1304, 1306, 1310, 1312 of the screen 1300.

Figure 14:
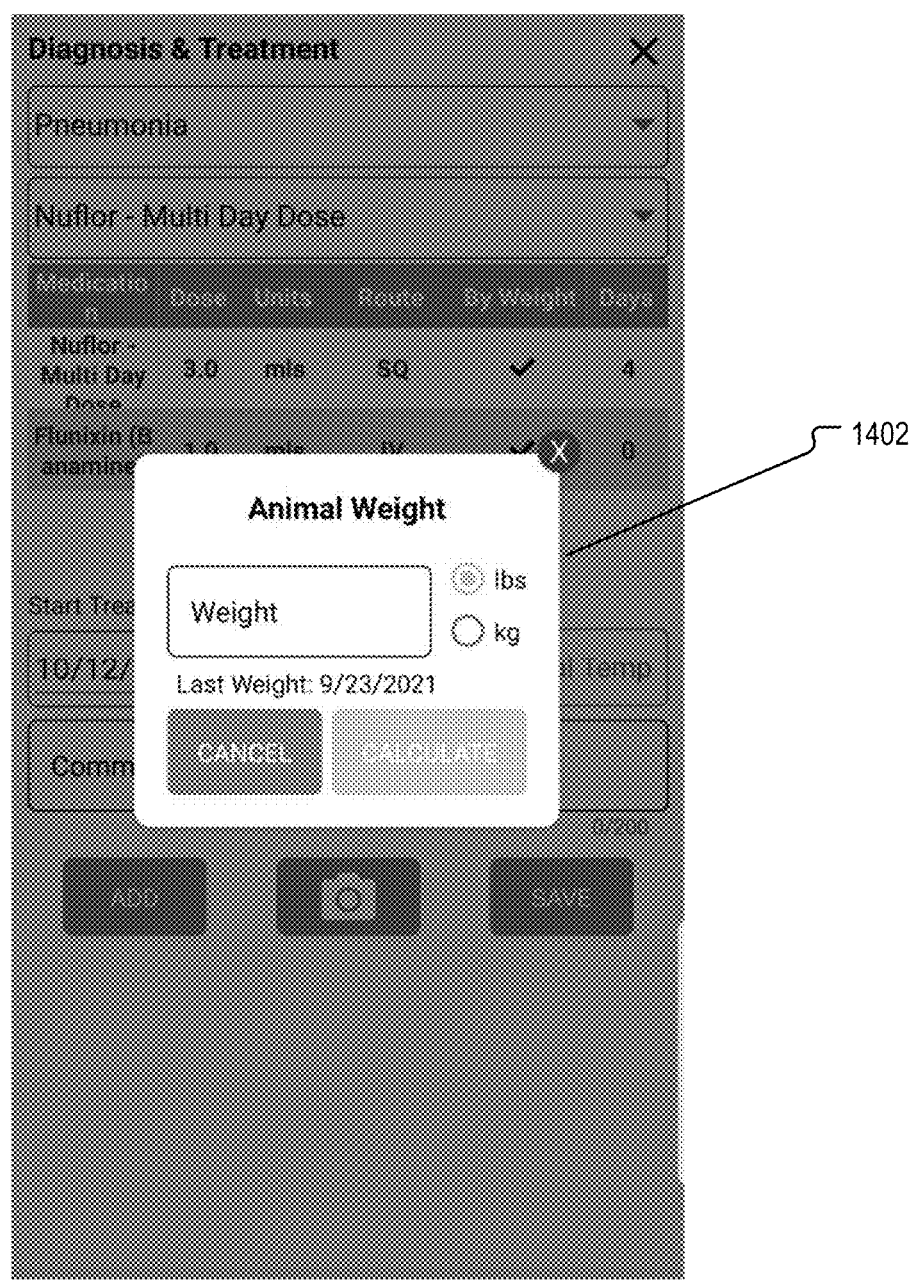

FIG. 14 shows an example of the screen 1300 including a dose data entry field 1402. The dose data entry field 1402 receives a weight of the animal. Selection of the Calculate button may prompt the user computing device to determine a dose of the treatment substance for the animal, for example, based on the animal weight entered at the dose data entry field 1402 and the treatment substance provided at the treatment substance entry field 1304.

Figure 15:
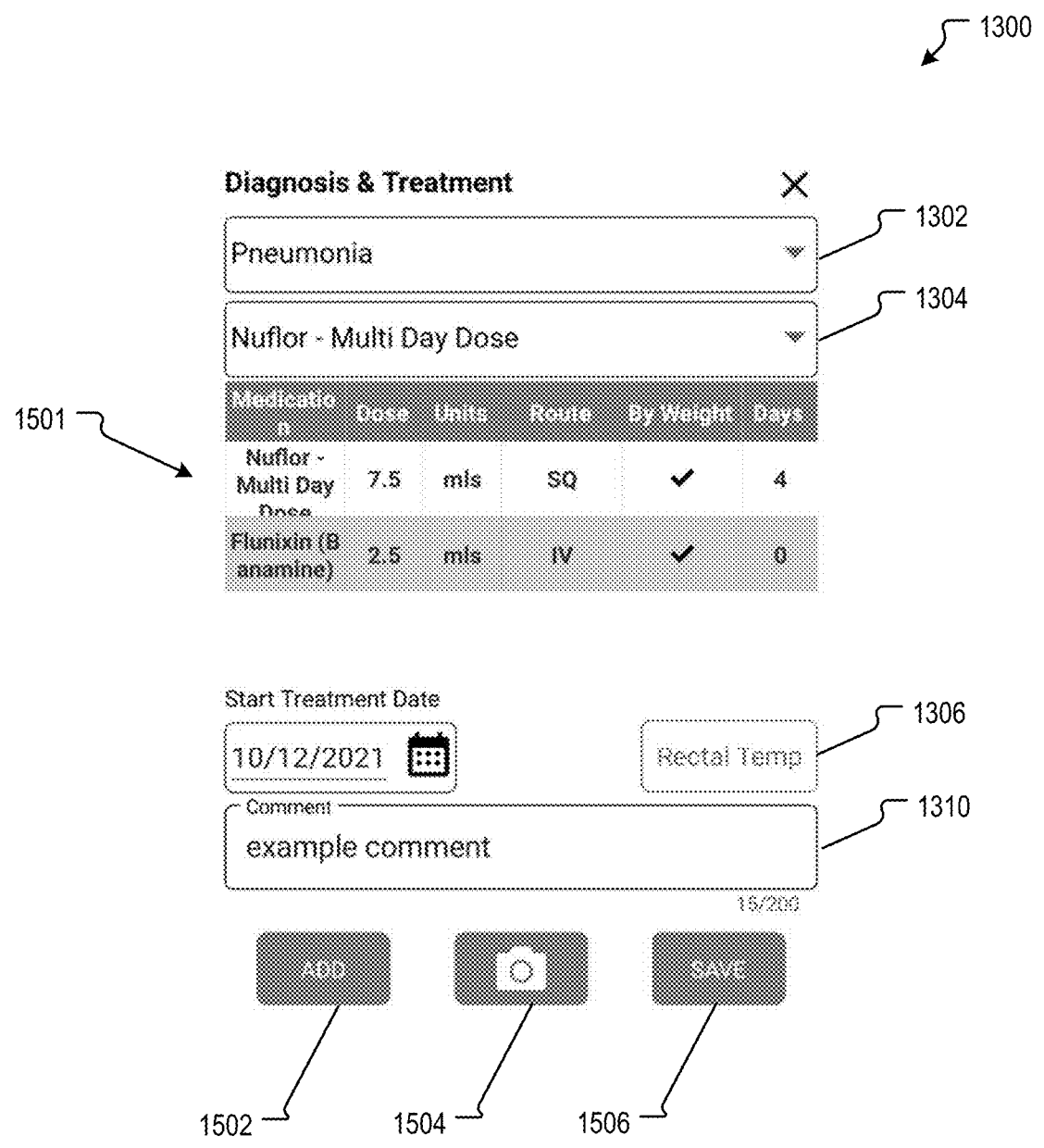

FIG. 15 shows another example of the screen 1300 including a dose field 1501. The dose field 1501 indicates a dose of one or more treatment substances to be provided to the animal. In this example, two treatment substances are to be provided to the animal. The dose field 1501 also indicates the delivery mechanism for the treatment substance, whether the dose was calculated by animal weight, and the duration of the course of treatment (in days).

FIG. 15 also shows example input elements 1502, 1504, 1506. An add button 1502 may be selected to add an additional treatment substance to be provided to the animal. For example, upon selecting the add button 1502, the livestock technician user may enter an additional treatment substance at the treatment substance entry field 1304, and may launch another instance of the dose data entry field 1402. A picture button 1504 may be selected to permit the livestock technician user to capture an image, for example, an image of the animal, an image of a graphical code on a treatment substance container, and/or the like. The image and/or information extracted from the image may be provided to the livestock management server as described herein. A save button 1506 may function as the actuation element, for example, similar to the save/submit button 144 of FIG. 1. When the livestock technician user selects the save button 1506, the user computing device may determine its current location and provide the current location along with other data about the animal, to the livestock management server.

Figure 16:
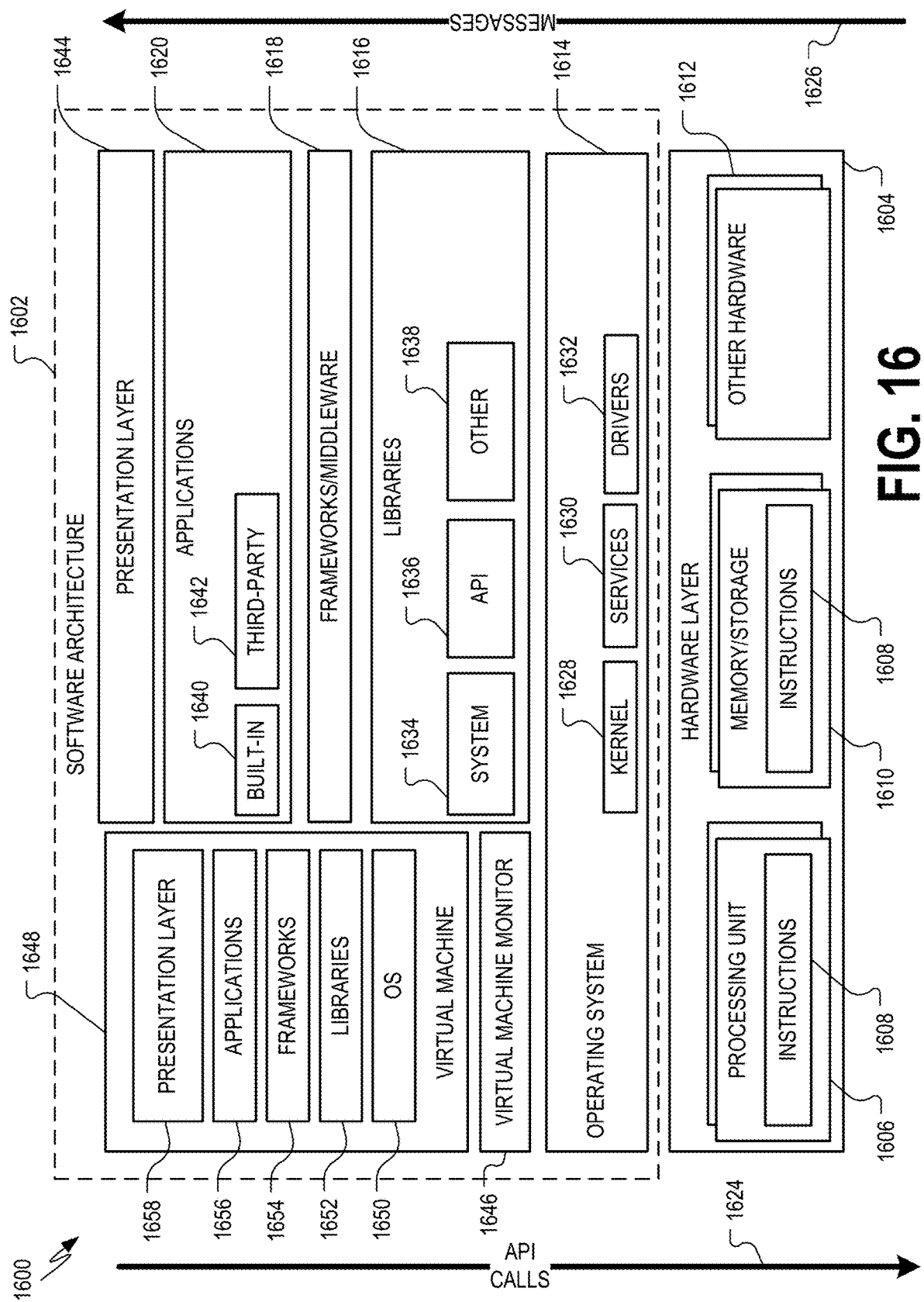
FIG. 16 is a block diagram showing one example of a software architecture for a computing device.

FIG. 16 is a block diagram 1600 showing one example of a software architecture 1602 for a computing device. The software architecture 1602 may be used in conjunction with various hardware architectures, for example, as described herein. FIG. 16 is merely a non-limiting example of a software architecture, and many other architectures may be implemented to facilitate the functionality described herein. A representative hardware layer 1604 is illustrated and can represent, for example, any of the above referenced computing devices. In some examples, the hardware layer 1604 may be implemented according to the architecture of the computer system of FIG. 16.

The representative hardware layer 1604 comprises one or more processing units 1606 having associated executable instructions 1608. Executable instructions 1608 represent the executable instructions of the software architecture 1602, including implementation of the methods, modules, subsystems, and components, and so forth described herein and may also include memory and/or storage modules 1610, which also have executable instructions 1608. Hardware layer 1604 may also comprise other hardware as indicated by other hardware 1612 which represents any other hardware of the hardware layer 1604, such as the other hardware illustrated as part of the architecture 1602.

In the example architecture of FIG. 16, the software architecture 1602 may be conceptualized as a stack of layers where each layer provides particular functionality. For example, the software architecture 1602 may include layers such as an operating system 1614, libraries 1616, frameworks/middleware 1618, applications 1620, and presentation layer 1644. Operationally, the applications 1620 and/or other components within the layers may invoke API calls 1624 through the software stack and access a response, returned values, and so forth illustrated as messages 1626 in response to the API calls 1624. The layers illustrated are representative in nature and not all software architectures have all layers. For example, some mobile or special purpose operating systems may not provide a frameworks/middleware 1618 layer, while others may provide such a layer. Other software architectures may include additional or different layers.

The operating system 1614 may manage hardware resources and provide common services. The operating system 1614 may include, for example, a kernel 1628, services 1630, and drivers 1632. The kernel 1628 may act as an abstraction layer between the hardware and the other software layers. For example, the kernel 1628 may be responsible for memory management, processor management (e.g., scheduling), component management, networking, security settings, and so on. The services 1630 may provide other common services for the other software layers. In some examples, the services 1630 include an interrupt service. The interrupt service may detect the receipt of an interrupt and, in response, cause the architecture 1602 to pause its current processing and execute an interrupt service routine (ISR) when an interrupt is accessed.

The drivers 1632 may be responsible for controlling or interfacing with the underlying hardware. For instance, the drivers 1632 may include display drivers, camera drivers, Bluetooth® drivers, flash memory drivers, serial communication drivers (e.g., Universal Serial Bus (USB) drivers), Wi-Fi® drivers, NFC drivers, audio drivers, power management drivers, and so forth depending on the hardware configuration.

The libraries 1616 may provide a common infrastructure that may be utilized by the applications 1620 and/or other components and/or layers. The libraries 1616 typically provide functionality that allows other software modules to perform tasks in an easier fashion than to interface directly with the underlying operating system 1614 functionality (e.g., kernel 1628, services 1630 and/or drivers 1632). The libraries 1616 may include system 1634 libraries (e.g., C standard library) that may provide functions such as memory allocation functions, string manipulation functions, mathematic functions, and the like. In addition, the libraries 1616 may include API libraries 1636 such as media libraries (e.g., libraries to support presentation and manipulation of various media format such as MPEG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1616 may also include a wide variety of other libraries 1638 to provide many other APIs to the applications 1620 and other software components/modules.

The frameworks 1618 (also sometimes referred to as middleware) may provide a higher-level common infrastructure that may be utilized by the applications 1620 and/or other software components/modules. For example, the frameworks 1618 may provide various graphic user interface (GUI) functions, high-level resource management, high-level location services, and so forth. The frameworks 1618 may provide a broad spectrum of other APIs that may be utilized by the applications 1620 and/or other software components/modules, some of which may be specific to a particular operating system or platform.

The applications 1620 includes built-in applications 1640 and/or third-party applications 1642. Examples of representative built-in applications 1640 may include, but are not limited to, a contacts application, a browser application, a book reader application, a location application, a media application, a messaging application, and/or a game application. Third party applications 1642 may include any of the built-in applications as well as a broad assortment of other applications. In a specific example, the third-party application 1642 (e.g., an application developed using the Android™ or iOS™ software development kit (SDK) by an entity other than the vendor of the particular platform) may be mobile software running on a mobile operating system such as iOS™, Android™, Windows® Phone, or other mobile computing device operating systems. In this example, the third-party application 1642 may invoke the API calls 1624 provided by the mobile operating system such as operating system 1614 to facilitate functionality described herein.

The applications 1620 may utilize built in operating system functions (e.g., kernel 1628, services 1630 and/or drivers 1632), libraries (e.g., system 1634, API libraries 1636, and other libraries 1638), and frameworks/middleware 1618 to create user interfaces to interact with users of the system. Alternatively, or additionally, in some systems interactions with a user may occur through a presentation layer, such as presentation layer 1644. In these systems, the application/module "logic" can be separated from the aspects of the application/module that interact with a user.

Some software architectures utilize virtual machines. In the example of FIG. 16, this is illustrated by virtual machine 1648. A virtual machine creates a software environment where applications/modules can execute as if they were executing on a hardware computing device. A virtual machine is hosted by a host operating system (operating system 1614) and typically, although not always, has a virtual machine monitor 1646, which manages the operation of the virtual machine as well as the interface with the host operating system (i.e., operating system 1614). A software architecture executes within the virtual machine such as an operating system 1650, libraries 1652, frameworks/middleware 1654, applications 1656 and/or presentation layer 1658. These layers of software architecture executing within the virtual machine 1648 can be the same as corresponding layers previously described or may be different.

Modules, Components and Logic

Certain embodiments are described herein as including logic or a number of components, modules, or mechanisms. Modules may constitute either software modules (e.g., code embodied (1) on a non-transitory machine-readable medium or (2) in a transmission signal) or hardware-implemented modules. A hardware-implemented module is a tangible unit capable of performing certain operations and may be configured or arranged in a certain manner. In example embodiments, one or more computer systems (e.g., a standalone, client, or server computer system) or one or more hardware processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or another programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses that connect the hardware-implemented modules). In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment, or a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., APIs).

Electronic Apparatus and System

Example embodiments may be implemented in digital electronic circuitry, or in computer hardware, firmware, or software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various example embodiments.

Example Machine Architecture and Machine-Readable Medium

Figure 17:
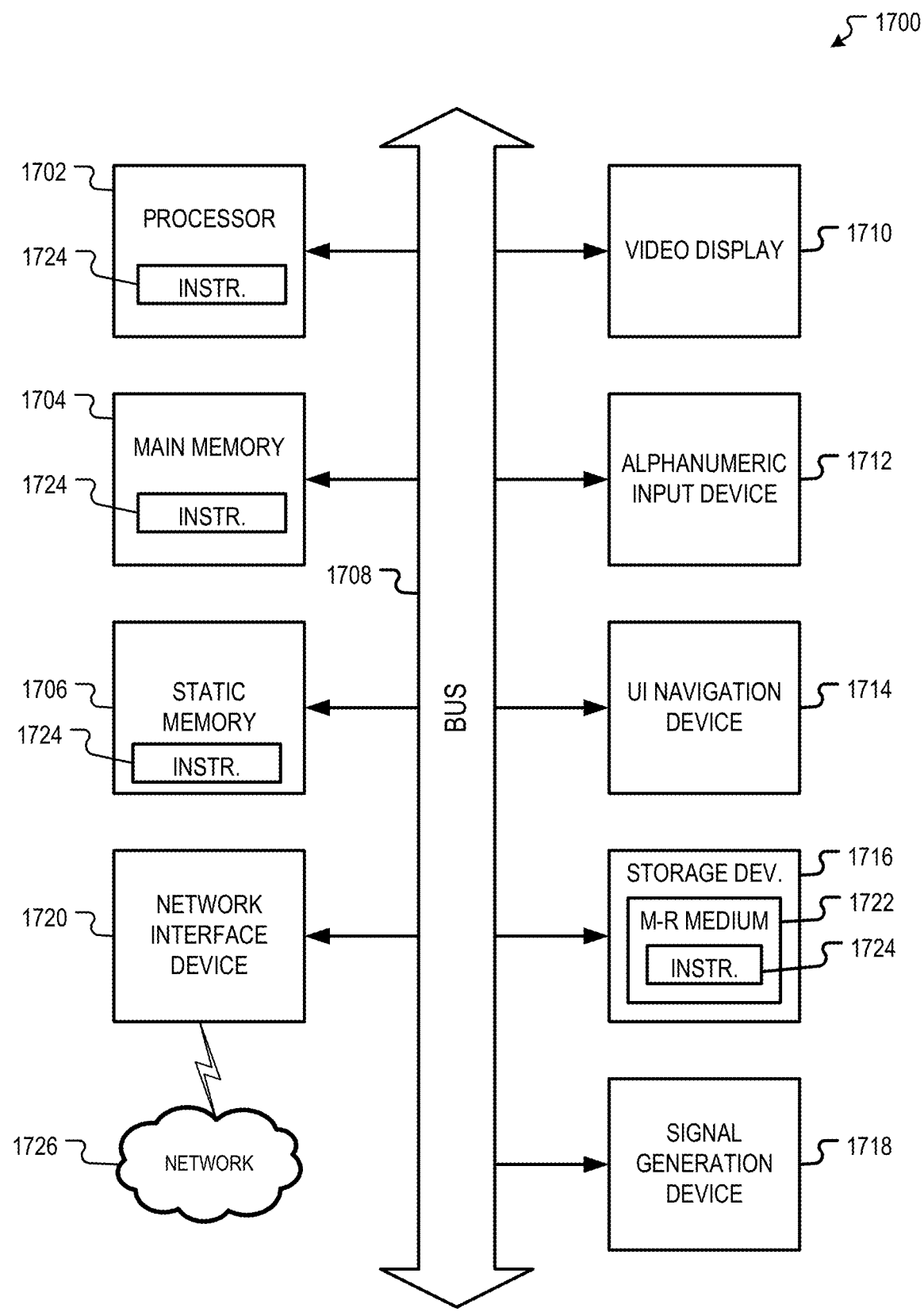
FIG. 17 is a block diagram of a machine in the example form of a computer system within which instructions may be executed for causing the machine to perform any one or more of the methodologies discussed herein.

FIG. 17 is a block diagram of a machine in the example form of a computer system 1700 within which instructions 1724 may be executed for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1700 includes a processor 1702 (e.g., a central processing unit (CPU), a graphics processing unit (GPU), or both), a main memory 1704, and a static memory 1706, which communicate with each other via a bus 1708. The computer system 1700 may further include a video display unit 1710 (e.g., a liquid crystal display (LCD) or a cathode ray tube (CRT)). The computer system 1700 also includes an alphanumeric input device 1712 (e.g., a keyboard or a touch-sensitive display screen), a user interface (UI) navigation (or cursor control) device 1714 (e.g., a mouse), a disk drive unit 1716, a signal generation device 1718 (e.g., a speaker), and a network interface device 1720.

Machine-Readable Medium

The disk drive unit 1716 includes a machine-readable media 1722 on which is stored one or more sets of data structures and instructions 1724 (e.g., software) embodying or utilized by any one or more of the methodologies or functions described herein. The instructions 1724 may also reside, completely or at least partially, within the main memory 1704 and/or within the processor 1702 during execution thereof by the computer system 1700, with the main memory 1704 and the processor 1702 also constituting machine-readable media 1722.

While the machine-readable medium 1722 is shown in an example embodiment to be a single medium, the term "machine-readable medium" may include a single medium or multiple media (e.g., a centralized or distributed database, and/or associated caches and servers) that store the one or more instructions 1724 or data structures. The term "machine-readable medium" shall also be taken to include any tangible medium that is capable of storing, encoding, or carrying instructions 1724 for execution by the machine and that cause the machine to perform any one or more of the methodologies of the present disclosure, or that is capable of storing, encoding, or carrying data structures utilized by or associated with such instructions 1724. The term "machine-readable medium" shall accordingly be taken to include, but not be limited to, solid-state memories, and optical and magnetic media. Specific examples of machine-readable media 1722 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and CD-ROM and DVD-ROM disks.

Transmission Medium

The instructions 1724 may further be transmitted or received over a communications network 1726 using a transmission medium. The instructions 1724 may be transmitted using the network interface device 1720 and any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., WiFi and WiMax networks). The term "transmission medium" shall be taken to include any intangible medium that is capable of storing, encoding, or carrying instructions 1724 for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the disclosure. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This detailed description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computerized system for providing a treatment substance to an animal, the system comprising:
    one or more user computing devices having a user computing device graphical user interface for accepting user input, a user computing device processor, Global Positioning System (GPS) device, and instructions stored on non-transitory machine-readable medium executable to: i) determine and send a first current location of the user computing device and ii) send treatment data entered through the user computing device graphical user interface; wherein treatment data is entered through the user computing device at the time treatment is administered to an animal;
    a livestock management server having at least one processor, and instructions stored on non-transitory machine-readable medium executable to: i) receive from a first of the one of the one or more user computing devices, an indication of the animal to be treated; ii) access an indication of a treatment substance to be provided to the animal; iii) receive from the first user computing device, a first current location iv) determine that the first current location of the first user computing device is more than a threshold distance from an expected location of the animal and v) generate an alert when the threshold distance is exceeded, wherein in response to an alert the location of the animal and the treatment administered are verified.

2. The system of claim 1, the operations further comprising:
    the user computing device graphical interface comprising:
    a treatment substance data entry field for receiving treatment data describing the treatment substance to be provided to the animal; and
    an initiate input element selectable by a user of the user computing device to prompt the user computing device to perform operations comprising:
        determining the first current location of the user computing device; and
        sending the treatment data to the at least one processor, the treatment data received via the treatment substance data entry field; and
        sending the first current location of the user computing device to the at least one processor.

3. The system of claim 1, wherein the indication of the treatment substance comprises graphical code data received from a treatment substance container.

4. The system of claim 1, wherein the indication of the animal comprises data received from an in vivo bolus associated with the animal.

5. The system of claim 1, further comprising:
    generating an animal treatment data block using the indication of the treatment substance and the first current location of the user computing device; and
    adding the animal treatment data block to an animal treatment blockchain data structure.

6. The system of claim 1, further comprising sending an alert message to an administrative user device based on the determination that the first current location of the user computing device is more than the threshold distance from the expected location of the animal, wherein the alert message describes the treatment substance, the first current location of the user computing device and the expected location of the animal.

7. The system of claim 1, further comprising storing the indication of the treatment substance and the first current location of the user computing device with timestamp data, the timestamp data indicating a first time when the first current location was received from the user computing device.

8. The system of claim 1, further comprising receiving, from an animal locator device, a sensed location of the animal, the sensed location of the animal being the expected location of the animal.

\* \* \* \* \*